US006476065B2

(12) United States Patent
Gunasekera et al.

(10) Patent No.: US 6,476,065 B2
(45) Date of Patent: Nov. 5, 2002

(54) DISCALAMIDE COMPOUNDS AND THEIR USE AS ANTI-PROLIFERATIVE AGENTS

(75) Inventors: Sarath P. Gunasekera, Vero Beach, FL (US); Ross E. Longley, Vero Beach, FL (US); Gopal K. Paul, Ft. Pierce, FL (US); Richard A. Isbrucker, Ontario (CA); Shirley A. Pomponi, Ft. Pierce, FL (US)

(73) Assignee: Harbor Branch Oceanographic Institution, Inc., Fort Pierce, FL (US)

( * ) Notice: Subject to any disclaimer, the term of this patent is extended or adjusted under 35 U.S.C. 154(b) by 0 days.

(21) Appl. No.: 09/835,692

(22) Filed: Apr. 16, 2001

(65) Prior Publication Data

US 2002/0016357 A1 Feb. 7, 2002

Related U.S. Application Data

(60) Provisional application No. 60/197,301, filed on Apr. 14, 2000.

(51) Int. Cl.[7] ...................... A61K 31/335; C07D 493/00
(52) U.S. Cl. ........................................ 514/452; 549/364
(58) Field of Search ........................... 549/364; 514/452

(56) References Cited

U.S. PATENT DOCUMENTS

| | | | |
|---|---|---|---|
| 4,206,221 A | 6/1980 | Miller et al. ................. | 424/278 |
| 4,801,606 A | 1/1989 | Higa et al. ................... | 514/452 |
| 4,808,590 A | 2/1989 | Higa et al. ................... | 514/272 |
| 4,868,204 A | 9/1989 | Blunt et al. .................. | 514/452 |
| 4,960,790 A | 10/1990 | Stella et al. ................. | 549/510 |
| 5,157,049 A | 10/1992 | Haugwitz et al. ........... | 514/449 |
| 5,476,953 A | 12/1995 | Clardy et al. ................ | 549/364 |

OTHER PUBLICATIONS

Burres, Neal S. and Jacob J. Clement (Jun. 1989) "Antitumor Activity and Mechanism of Action of the Novel Marine Natural Products Mycalamide–A and –B and Onnamide" Cancer Research 49:2935–2940.
Faulkner, D.J. (2001) Natural Products Reports 18:1–49.
Fusetani, Nobuhiro, Takeo Sugawara, Shigeki Matsunaga (1992) "Theopederins A–E, Potent Antitumor Metabolites from a Marine Sponge, Theonella sp." J. Org. chem. 57(14):3828–3832.
Fuchs, D.A. and R. K. Johnson (1978) "Cytologic Evidence That Taxol, an Antineoplastic Agent From Taxus brevifolia, Acts as a Mitotic Spindle Poison" Cancer Treatment Reports 62(8):1219–1222.
Gunasekera, S.P., M. Gunasekera, and R.E. Longley (1990) "Discodermolide: A New Bioactive Polyhydroxylated Lactone from the Marine Sponge Discodermia dissoluta" J. Org. Chem. 55:4912–4915.
Gunasekera, Sarath P., Malika Gunasekera, Ross E. Longley, Gayle K. Schulte (1991) J. Org. Chem. 56:1346 (Correction to above).
Hong, Chang Yong and Yoshito Kishi (1990) "Total Synthesis of Mycalamides A and B" J. Org. Chem 55:4242–4245.

Hong, Chang Yong and Yoshito Kishi (1991) "Total Synthesis of Onnamide A" J. Am. Chem. Soc. 113:9693–9694.
Hung, Deborah T., Jennie B. Nerenberg and Stuart L. Schreiber (1994) "Distinct binding and cellular properties of synthetic (+)–and (–)–Discodermolides" Chemistry & Biology 1(1):67–71.
Hung, Deborah T., Jie Chen, Stuart L. Schreiber (1996) "(+)–Discodermolide binds to microtubules in stoichiometric ratio to tubulin dimers, blocks taxol binding and results in mitotic arrest" Chemistry & Biology 3(4):287–293.
Matsumoto, Takeshi, Mitsutoshi Yanagiya, Sawae Maeno and Seiichi Yasuda (1968) "A Revised Structure of Pederin" Tetrahedron Letters 60:6297–6300.
Matsunaga, Shiegki, Nobuhiro Fusetani and Youichi Nakao (1992) "Eight New Cytotoxic Metabolites Closely Related to Onnamide A from Two Marine Sponges of the Genus Theonella" Tetrahedron 48(39):8369–8376.
Minale, L. et al. [1979] "Natural Products from Porifera" Fortschr Chem. Org. Naturst. 33:1–72.
Perry, Nigel B., John W. Blunt, Murray H.G. Munro (1988) "Mycalamide A, and Antiviral Compound from a New Zealand Sponge of the Genus Mycale" J. Am. Chem. Soc. 110:4850–4851.
Rowinsky, Eric K. and Ross C. Donehower (Apr. 1995) "Drug Therapy" The New England Journal of Medicine 332(15):1004–1014.
Sakemi,Shinichi, Toshio Ichiba, Shigeo Kohmoto and Gabriel Saucy (1988) "Isolation and Structure Elucidation of Onnamide A, a New Bioactive metabolite of a Marine Sponge, Theonella sp." J. Am. Chem. Soc. 110:4851–4853.
Schiff, Peter B., Jane Fant, and Susan B. Horwitz (1979) "Promotion of Microtubule assembly in vitro by taxol" Nature (London) 22:665–667.
Tsukamoto, Sachiko, Shigeki Matsunaga, Nobuhiro Fusetani, Akio Toh–e (1999) "Theopederins F–J: Five New Antifungal and Cytotoxic Metabolites from the Marine Sponge, Theonella swinhoei" Thetrahedron 55:13697–13702.
Uemura, Daisuke, Kanji Takahashi, Toshihiro Yamamoto (1985) "Norhalichondrin A: An Antitumor Polyether Macrolide from a Marine Sponse" J. Am. Chem. Soc. 1985, 107:4796–4798.
Fukui, H. et al. (Aug. 19, 1997) "Synthesis and biological activity of artifiicial analogs of mycalamide A" Bioorgan & Medicinal Chemistry Letters, GB, Oxford 7(16):2081–2086.

Primary Examiner—Amelia Owens
(74) Attorney, Agent, or Firm—Saliwanchik, Lloyd & Saliwanchik

(57) ABSTRACT

The subject invention provides novel biologically active compounds which are useful for inhibiting cellular proliferation. Because of the biological activity of these compounds, they can be used for immunomodulation and/or treating cancer. In a preferred embodiment, the novel compounds, compositions and methods of use of the subject invention can advantageously be used to inhibit the growth of tumor cells in a mammalian host. More particularly, the subject compounds can be used for inhibiting in a human the growth of tumor cells, including cells of breast, colon, CNS, ovarian, renal, prostate, bone, gastrointestinal, stomach, testicular, or lung tumors, as well as human leukemia or melanoma cells. Specifically exemplified are discalamides A and B.

41 Claims, 6 Drawing Sheets

DISCALAMIDE COMPOUNDS AND THEIR USE AS ANTI-PROLIFERATIVE AGENTS

CROSS REFERENCE TO A RELATED APPLICATION

This application claims priority from provisional patent application U.S. Ser. No. 60/197,301, filed Apr. 14, 2000.

The subject invention was made with government support under a research project supported by National Institute of Health/National Cancer Institute Grant No. 1RO1-CA 74227. The government has certain rights in this invention.

BACKGROUND OF INVENTION

Of great importance to man is the control of pathological cellular proliferation such as that which occurs in the case of cancer. Considerable research and resources have been devoted to oncology and antitumor measures including chemotherapy. While certain methods and chemical compositions have been developed which aid in inhibiting, remitting, or controlling the growth of, for example, tumors, new methods and antiproliferative chemical compositions are needed.

In searching for new biologically active compounds, it has been found that some natural products and organisms are potential sources for chemical molecules having useful biological activity of great diversity. For example, the diterpene commonly known as Taxol, isolated from several species of yew trees, is a mitotic spindle poison that stabilizes microtubules and inhibits their depolymerization to free tubulin (Fuchs, D. A., R. K. Johnson [1978] *Cancer Treat. Rep.* 62:1219–1222; Schiff, P. B., J. Fant, S. B. Horwitz [1979] *Nature* (London) 22:665–667). Taxol is also known to have antitumor activity and has undergone a number of clinical trials which have shown it to be effective in the treatment of a wide range of cancers (Rowinski, E. K. R. C. Donehower [1995] *N. Engl. J. Med* 332:1004–1014). See also, e.g., U.S. Pat. Nos. 5,157,049; 4,960,790; and 4,206,221.

Marine sponges have also proven to be a source of biologically active chemical molecules. A number of publications disclose organic compounds derived from marine sponges including Scheuer, P. J. (ed.) *Marine Natural Products, Chemical and Biological Perspectives,* Academic Press, New York, 1978–1983, Vol. I–V; Uemura, D., K. Takahashi, T. Yamamoto, C. Katayama, J. Tanaka, Y. Okumura, Y. Hirata [1985] *J. Am. Chem. Soc.* 107:4796–4798; Minale, L. et al. [1976] *Fortschr. Chem. Org. Naturst.* 33:1–72; Faulkner, D. J. [2001] *Natural Products Reports* 18:1–49; Gunasekera, S. P., M. Gunasekera, R. E. Longley and G. K. Schulte [1990] "Discodermolide: A new bioactive polyhydroxy lactone from the marine sponge *Discodermia dissoluta*" *J. Org. Chem.,* 55:4912–4915; [1991] *J. Org. Chem.* 56:1346; Hung, Deborah T., Jenne B. Nerenberg, Stuart Schreiber [1994] "Distinct binding and cellular properties of synthetic (+)- and (–) discodermolides" *Chemistry and Biology* 1:67–71; Hung, Deborah T., Jie Cheng, Stuart Schreiber [1996] (+)-Discodermolide binds to microtubules in stoichiometric ratio to tubulin dimers, blocks Taxol binding and results in mitotic arrest" *Chemistry and Biology* 3:287–293. U.S. Pat. No. 4,801,606 and 4,808,590 (T. Higa, S. Sakemi and S. Cross) disclose related onnamide compounds, having antiviral, antitumor, and antifungal properties, isolated from the marine sponge Theonella sp.

Mycalamides A and B have been isolated from a New Zealand sponge Mycale sp. See, Mycalamide A, an antiviral compound from a New Zealand sponge of the genus Mycale. N. B. Perry, J. W. Blunt, M. H. G. Munro and L. K. Pannell. *J. Amer. Chem. Soc.,* [1988] 110, 4850–4851 and Mycalamide compounds, compositions, thereof and methods of preparation and use, U.S. Pat. No. 4,868,204, J. W. Blunt, M. H. G. Munro, N. B. Perry, A. M. Thompson. Pederin, a related compound was isolated from a blister beetle *Paederus fuscipes.* Onnamide A was first isolated from an Okinawan sponge of the genus Theonella. Subsequently, a University of Tokyo group reported the isolation of related metabolites, viz. 13-des-O-methylonnamide A, dihydroonnamide A, onnamides B, C, D and E, and 17-oxo-onnamide B from the Hachijo-jima Island sponge *Theonella swinhoei* and pseudoonnamide A from a morphologically different sponge of the genus Theonella. (see, Isolation and structure elucidation of onnamide A, a new bioactive metabolite of a marine sponge, Theonella sp., S. Sakemi, T. Ichiba, S. Kohmoto, G. Saucy and T. Higa, *J. Am. Chem. Soc.,* [1988] 110, 4851–4853; Antitumor activity and mechanism action of the novel marine natural products mycalamides A and B and onnamides. N. S. Burres and J. J. Clement, *Cancer Research* [1989] 49, 2935–2940; S. Matsunaga, N. Fusetani and Y. Nakao, *Tetrahedron* [1992] 48, 8369; and T. Matsumoto, M. Yanagiya, S. Maeno, S. Yasuda, *Tetrahedron Lett.,* [1968] 6297). In 1992, Fusetani et al., reported related compounds, theopederins A–E also isolated from the sponge, Theonella sp. (*J. Org Chem,* [1992] 57, 3828–3832). Recently in 1999, the same group reported theopederins F–J. also isolated from the sponge, *Theonella swinhoei* (*Tetrahedron* [1999] 55, 13697–13702). The discalamides are structurally related to the theopederins but not identical to any known theopederins. Discalamide A has an extra double bond and a methoxy group as compared to theopederin G. Similarly, discalamide B has an extra double bond as compared to theopederin G. Therefore, discodermolides A and B are trivially named theopederins K and L, respectively.

BRIEF SUMMARY

A principal object of the subject invention is the provision of novel compositions of biologically active compounds. These compounds have been found to have potent antiproliferative activity. Because of this antiproliferative activity, the compounds of the subject invention can advantageously be used for immunomodulation and/or treating cancer.

Specifically exemplified herein are discalamides A and B and various analogs and derivatives of these compounds. Advantageously, these compounds possess potent activity against P388 and A459 tumor cells. These activities are at least the equivalent of, and at times surpass, the cytotoxic properties of such marine compounds as onnamide A, mycalamides A and B, lasonolide A, discodermolide and the ecteinascidins (729 and 743).

The compounds of the subject invention can be isolated from the sponge, Discodermia sp. Synthetic schemes have been worked out for many of this class of compounds, and such methodologies can be applied to the synthesis of discalamides A and B, and to various analogs and derivatives thereof (C. Y. Hong and Y. Kishi, *J. Org. Chem.* [1990] 55, 4242; C. Y. Hong and Y. Kishi, *J. Am. Chem. Soc.* [1991] 113, 9693).

In a specific embodiment, the novel compositions and methods of the subject invention can be used in the treatment of an animal hosting cancer cells including, for example, inhibiting the growth of tumor cells in a mammalian host. More particularly, the subject compounds can be used for inhibiting in a human the growth of tumor cells, including cells of breast, colon, CNS, ovarian, renal, prostate, bone, gastrointestinal, stomach, testicular, or lung tumors, as well as human leukemia or melanoma cells.

In accordance with the subject invention, methods for inhibiting tumors in a host include contacting tumor cells with an effective amount of the new pharmaceutical compositions of the invention. The tumor cells inhibited by the invention are those which are susceptible to the subject compounds described herein or compositions comprising those compounds. Additional aspects of the invention include the provision of methods for producing the new compounds and compositions.

Other objects and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

DETAILED DISCLOSURE

The subject invention provides novel biologically active compounds that are useful for inhibiting cellular proliferation. Because of the biological activity of these compounds, they can be used for immunomodulation and/or treating cancer. In a preferred embodiment, the novel compounds, compositions and methods of use of the subject invention can advantageously be used to inhibit the growth of tumor cells in a mammalian host. More particularly, the subject compounds can be used for inhibiting in a human the growth of tumor cells, including cells of breast, colon, CNS, ovarian, renal, prostate, bone, gastrointestinal, stomach, testicular, or lung tumors, as well as human leukemia or melanoma cells.

Figure 1A:
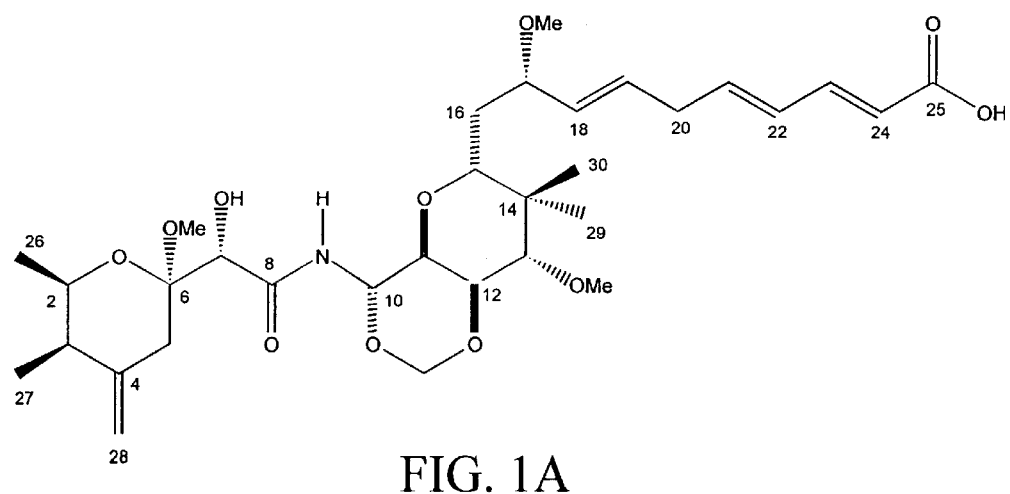
FIG. 1A shows the structure of discalamide A(I).
Figure 1B:
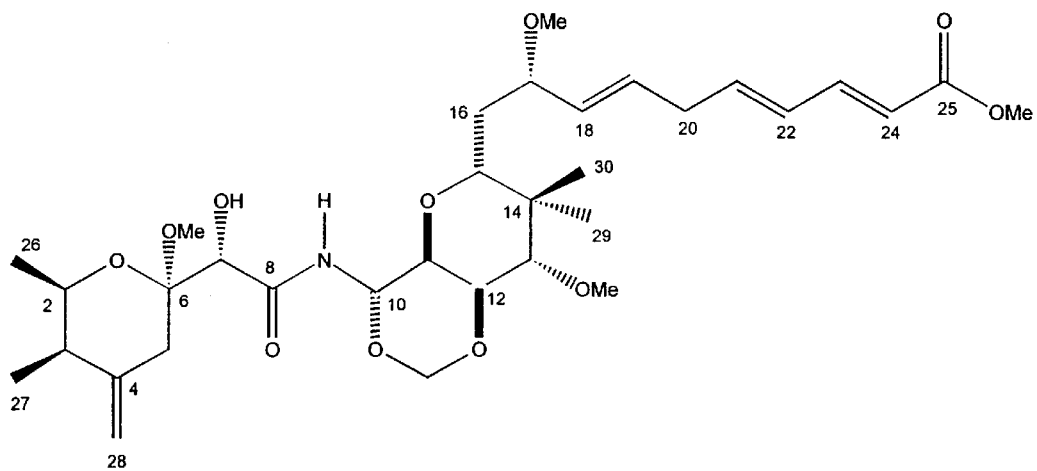
FIG. 1B shows the structure of discalamide A methylester (III).
Figure 1C:
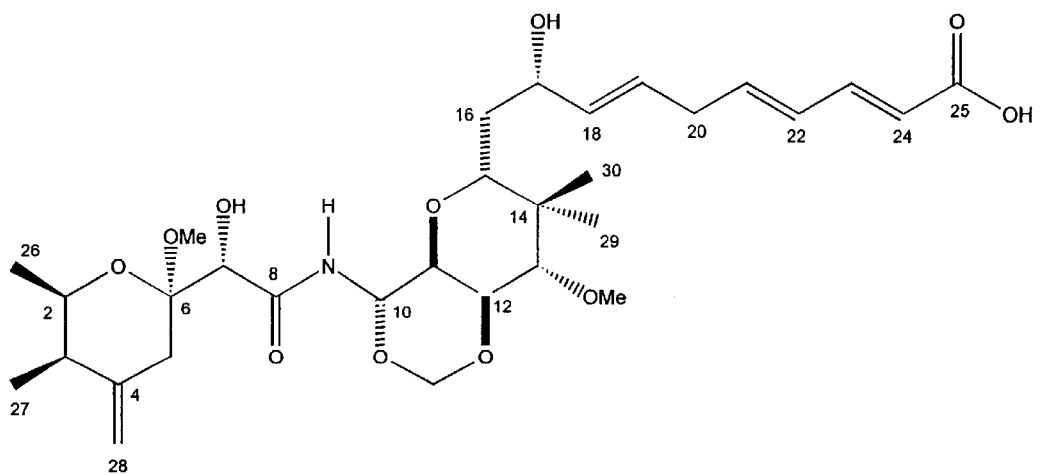
FIG. 1C shows the structure of discalamide B(II).

Specifically exemplified herein are discalamide A (I), discalamide A methyl ester (III), and discalamide B (II). The structures of these compounds are shown in FIGS. 1A–1C. The subject invention also concerns various analogs and derivatives of these compounds.

The discalamides of the subject invention can be isolated from the marine sponge Discodermia sp. (Phylum Porifera, Class Demospongiae, Order Lithistida, Family Theonellidae). The morphology of the sponge varies from club-shaped to lobate to knob-shaped. It is firm in consistency. The color is cream with tinges of pink or brown when alive, fading to white when preserved in ethanol. The spicule skeleton consists of desmas, discotriaenes, oxeotes, microxea, and acanthose microrhabds, as described in the literature (e.g., Van Soest, R. W. M. and Stentoft, N. 1988. Barbados deep-water sponges. Studies on the Fauna of Curacao and Other Caribbean Islands: No. 215, Vol. LXX, pp. 50–52.) Taxonomic reference samples have been deposited in the Harbor Branch Oceanographic Museum, catalog numbers 003:00977, 003:00978, 003:00979, and 003:00980. The taxonomic reference samples were collected by manned submersible off the north coast of Honduras (latitude 16°24.847'N, longitude 85°58.575'W, depth 440 ft; latitude 16°25.342'N, longitude 85°58.477'W, depth 405 ft; latitude 16°25.394'N, longitude 85°58.397'W, depth 415 ft; and latitude 16°25.394'N, longitude 85°58.397'W, depth 415 ft, respectively). Thus, one method of preparation for the compounds used according to the subject invention involves extraction from marine sponges of the Genus Discodermia.

Figure 2A:
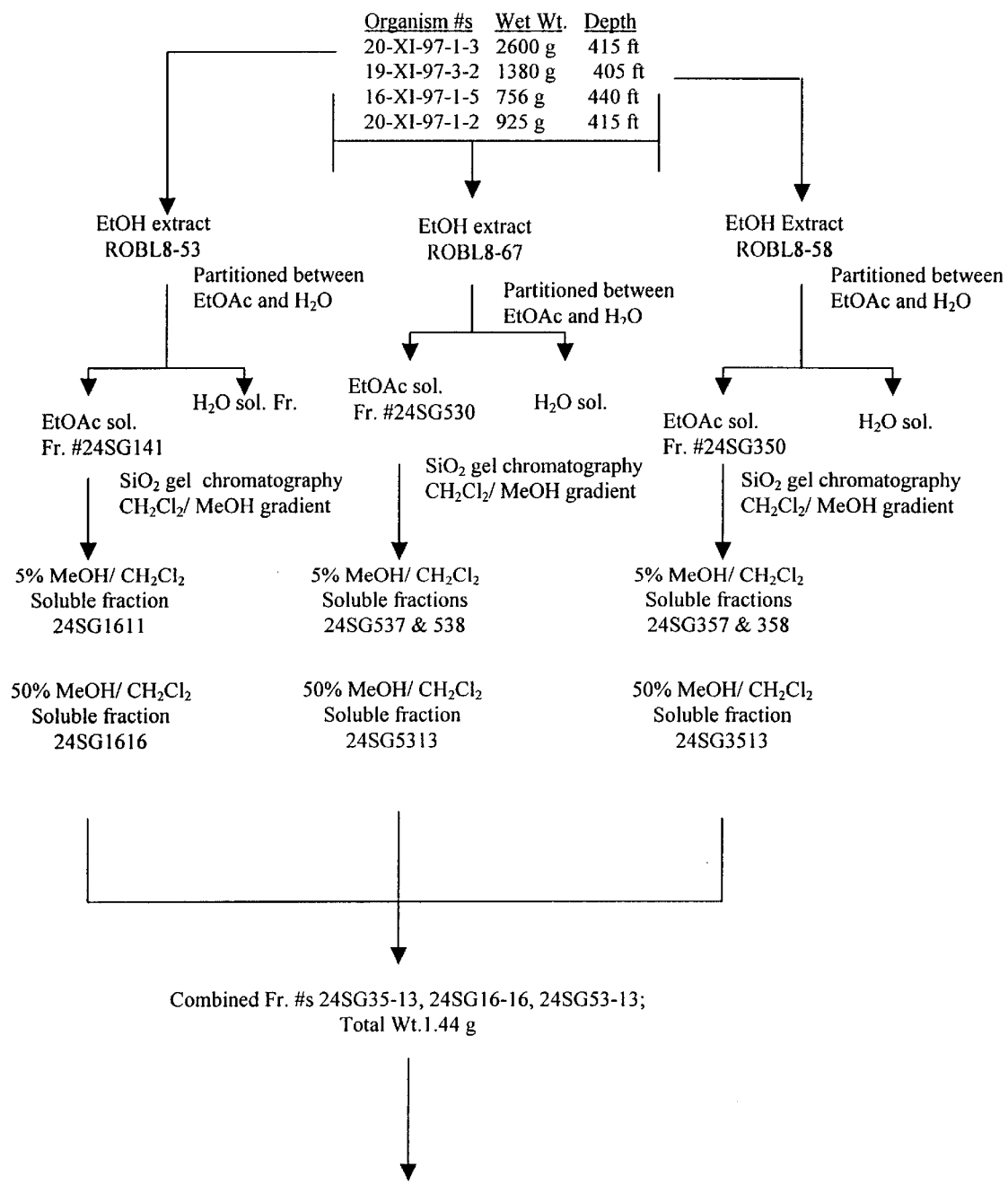
FIGS. 2A and 2B show a preferred extraction scheme for isolating compounds of the subject invention.
Figure 2B:
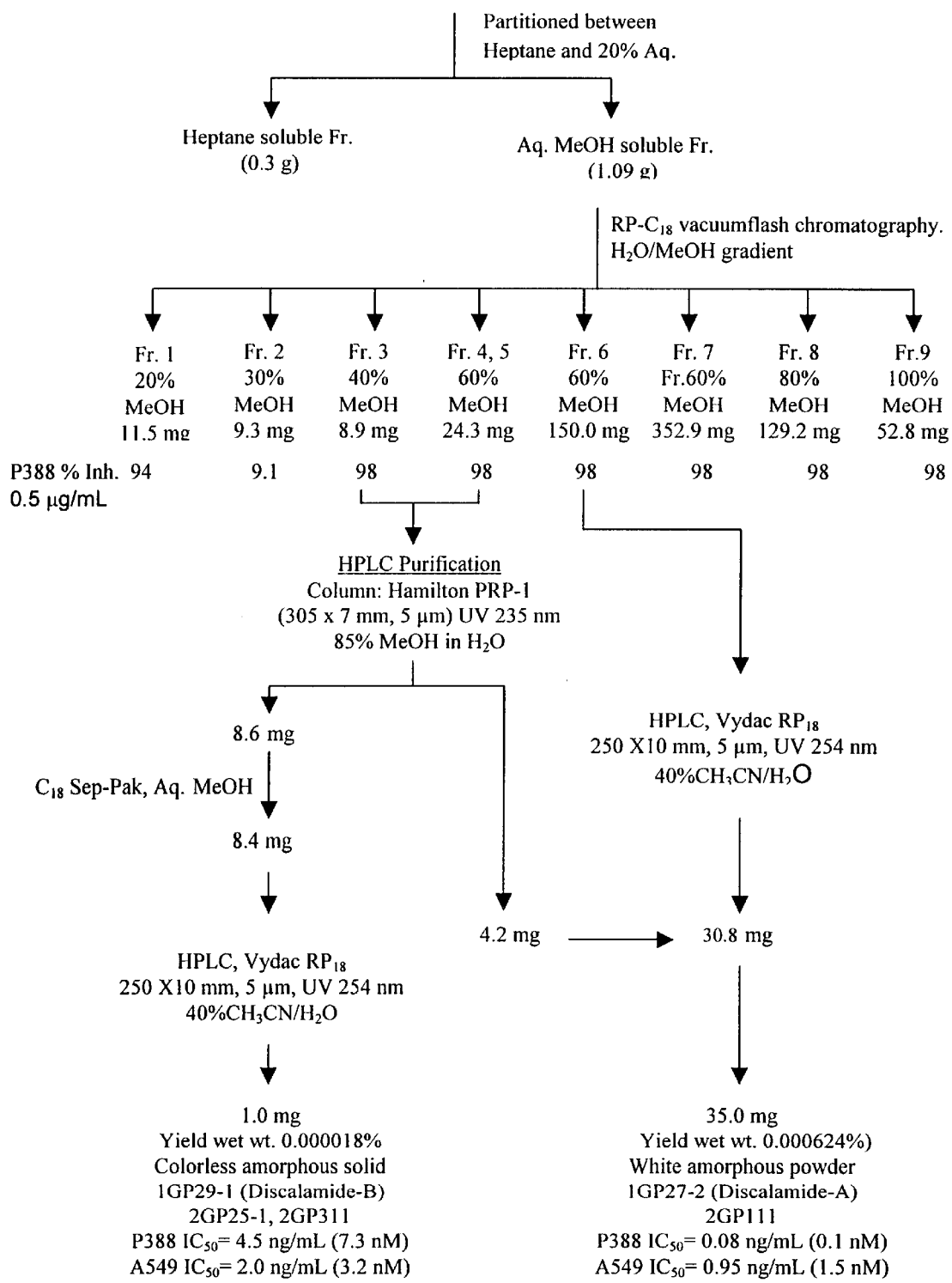

Compounds of the invention can be isolated by various liquid-liquid fractionation followed by chromatographic techniques from marine sponge extracts. Isolation procedures include various chromatography techniques, e.g., column chromatography with suitable columns, including silica, C-18, CN and amino columns. A variety of solvents are available for use as single or mixed eluents, such as methylene chloride, methanol, ethyl acetate, acetonitrile, n-propanol, n-butanol, water, and equivalent solvents. Preferred isolation techniques for further purification include chromatographic operations such as high-performance liquid chromatography with suitable columns with suitable solvent, particularly, methylene chloride/methanol or methanol/water mixtures. Preferred extraction details are shown in FIGS. 2A and 2B.

Skilled chemists having the benefit of the instant disclosure, can readily use procedures to purify the subject compounds. In carrying out such operations, suitable filtration, chromatographic and other purification techniques can be used. These techniques could include, for example, reversed phase (RPLC), column, vacuum flash, medium pressure (MPLC) and high performance liquid chromatography (HPLC) with a suitable column such as silica gel, Sephadex LH-20, ammonia-treated silica gel, bonded phase RP-18, RP-8, cyano and amino columns. Such columns are eluted with suitable solvents as discussed above. With a knowledge of the compounds of the subject invention, and their structures, skilled chemists can use known procedures to synthesize these compounds from available substrates.

Isolation of discalamides is the first report of this class of monoamide compounds from the sponge genus Discodermia. This class of compounds is characterized by the presence of the acid moiety, 2-hydroxy-3-methoxy-5-exomethylene-6-methyl-3,7-oxooctanoic acid, that forms the amide linkage. These compounds have structural similarities to the known heterocyclic monoamides, mycalamide and pederin, and the diamides, onnamides, but are new and advantageous chemical entities. Discalamides show potent biological activity against A549 human lung adenocarcinoma and P388 murine leukemia cell lines compared to the reported compounds, mycalamides and onnamides (Table 1) and theopederins Fusetani et al., *J. Org Chem* [1992] 57, 3828; Fusetani et al. *Tetrahedron* [1999] 55, 13697).

TABLE 1

| Compound | P388 $IC_{50}$ | A549 $IC_{50}$ |
| --- | --- | --- |
| Onnamide A | 2.4 nM | 170 nM |
| Mycalamide A | 5.2 nM | 3.6 nM |
| Mycalamide B | 1.3 nM | 0.6 nM |
| Lasonolide A | 2.8 nM | 57 nM |
| Discodermolide | 55 nM | 25 nM |
| Ecteinascidin 729 | 1.2 nM | Not Determined |
| Ecteinascidin 743 | 1.7 nM | Not Determined |
| 2GP111 (Discalamide A) | 0.1 nM | 1.5 nM |

TABLE 1-continued

| Compound | P388 IC$_{50}$ | A549 IC$_{50}$ |
|---|---|---|
| 2GP313 (Discalamide A-methylester) | 0.3 nM | 0.8 nM |
| 2GP311 (Discalamide B) | 7.3 nM | 3.2 nM |

In further embodiments of the subject invention, salts within the scope of the invention are made by adding mineral acids, e.g., HCl, H$_2$SO$_4$, or strong organic acids, e.g., formic, oxalic, citric and tartaric acids in appropriate amounts to form the acid addition salt of the parent compound or its derivative. Thus, the compounds of the subject invention include the salts of the exemplified structures. These salts may be for example, the sodium, potassium, and calcium salts. Also, synthesis type reactions may be used pursuant to known procedures to add or modify various groups in the preferred compounds to produce other compounds within the scope of the invention.

The scope of the invention is not limited by the specific examples and suggested procedures and uses related herein since modifications can be made within such scope from the information provided by this specification to those skilled in the art.

The subject invention pertains also to analogs and derivatives of discalamides A and B, and to the use of these analogs and derivatives of discalamides A and B as antiproliferative agents. As used herein, the terms "analogs" and "derivatives" refer to compounds which are substantially the same as another compound but which may have been modified by, for example, adding additional side groups. Analogs and derivatives of the subject invention include the following:

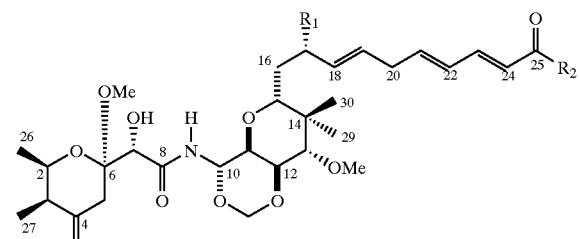

R$_1$ = OX, where X = —A, —CH$_2$—Q, —COA or —COZ
R$_2$ = OA
A = lower alkyl
Q = phenyl, tolyl or xylyl
Z = monocyclic aryl Additional analogs and derivatives are shown below:

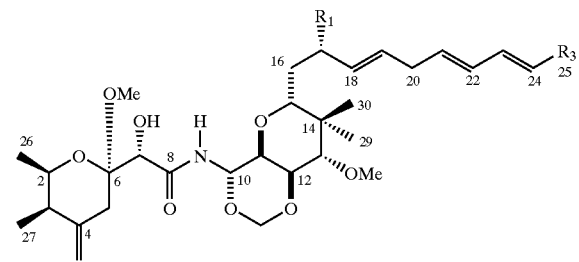

R$_1$ = OX, R$_3$ = CH$_2$OX where X = H, A, —CH$_2$—Q, —COA or COZ
A = lower alkyl
Q = phenyl, tolyl or xylyl
Z = monocyclic aryl Specifically exemplified herein are the following analogs and derivatives:

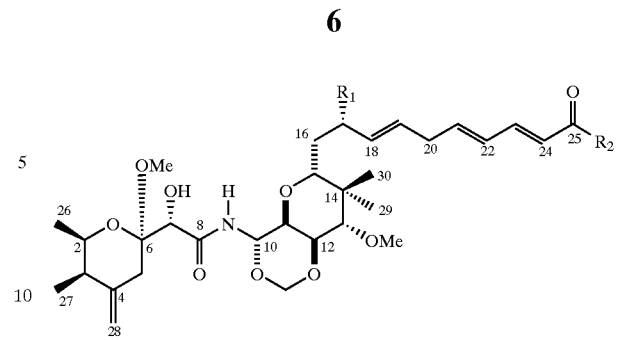

1 Discalamide A          R$_1$ = OMe, R$_2$ = OH
2 Discalamide B          R$_1$ = OH,  R$_2$ = OH
3 Discalamide A methylester   R$_1$ = OMe, R$_2$ = OMe
4 Discalamide B methylester   R$_1$ = OH,  R$_2$ = OMe
5 Discalamide A sodium salt   R$_1$ = OMe, R$_2$ = O$^-$Na$^+$
6 Discalamide B sodium salt   R$_1$ = OH,  R$_2$ = O$^-$Na$^+$
7 Discalamide A potassium salt R$_1$ = OMe, R$_2$ = O$^-$K$^+$
8 Discalamide B potassium salt R$_1$ = OH,  R$_2$ = O$^-$K$^+$

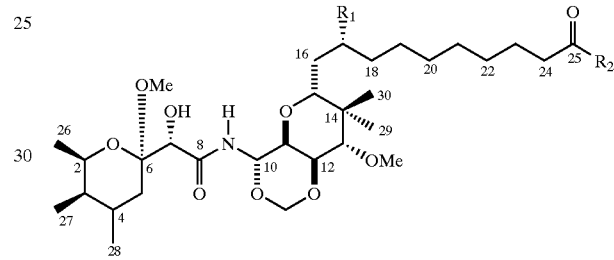

9 Octahydrodiscalamide A            R$_1$ = OMe, R$_2$ = OH
10 Octahydrodiscalamide B           R$_1$ = OH,  R$_2$ = OH
11 Octahydrodiscalamide A methylester  R$_1$ = OMe, R$_2$ = OMe
12 Octahydrodiscalamide B methylester  R$_1$ = OH,  R$_2$ = OMe
13 Octahydrodiscalamide A sodium salt  R$_1$ = OMe, R$_2$ = O$^-$Na$^+$
14 Octahydrodiscalamide B sodium salt  R$_1$ = OH,  R$_2$ = O$^-$Na$^+$
15 Octahydrodiscalamide A potassium salt R$_1$ = OMe, R$_2$ = O$^-$K$^+$
16 Octahydrodiscalamide B potassium salt R$_1$ = OH,  R$_2$ = O$^-$K$^+$

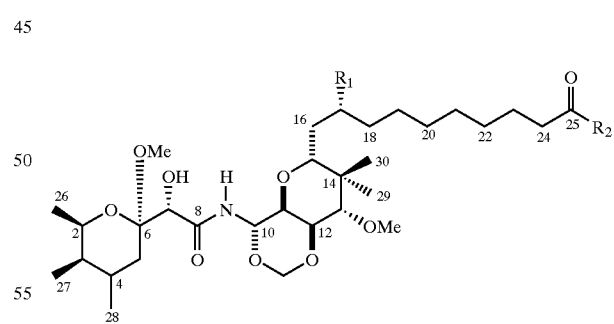

Δ4-28 or Δ18 or Δ21 or Δ23

17. Hexahydrodiscalamide A           R$_1$ = OMe, R$_2$ = OH
18. Hexahydrodiscalamide B           R$_1$ = OH,  R$_2$ = OH
19. Hexahydrodiscalamide A methylester R$_1$ = OMe, R$_2$ = OMe
20. Hexahydrodiscalamide B methylester R$_1$ = OH,  R$_2$ = OMe
21. Hexahydrodiscalamide A sodium salt R$_1$ = OMe, R$_2$ = O$^-$Na$^+$
22. Hexahydrodiscalamide B sodium salt R$_1$ = OH,  R$_2$ = O$^-$Na$^+$
23. Hexahydrodiscalamide A potassium salt R$_1$ = OMe, R$_2$ = O$^-$K$^+$
24. Hexahydrodiscalamide B potassium salt R$_1$ = OH,  R$_2$ = O$^-$K$^+$

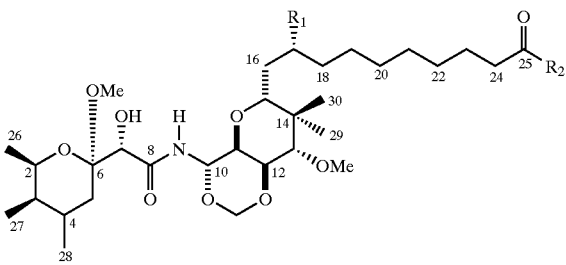

Δ4-28 or Δ18 or Δ21 or Δ23
Δ18 and Δ21 or Δ18 and Δ23 or Δ21 and Δ23

| | | |
|---|---|---|
| 25. Tretrahydrodiscalamide A | $R_1$ = OMe, | $R_2$ = OH |
| 26. Tretrahydrodiscalamide B | $R_1$ = OH, | $R_2$ = OH |
| 27. Tretrahydrodiscalamide A methylester | $R_1$ = OMe, | $R_2$ = OMe |
| 28. Tretrahydrodiscalamide B methylester | $R_1$ = OH, | $R_2$ = OMe |
| 29. Tretrahydrodiscalamide A sodium salt | $R_1$ = OMe, | $R_2$ = O$^-$Na$^+$ |
| 30. Tretrahydrodiscalamide B sodium salt | $R_1$ = OH, | $R_2$ = O$^-$Na$^+$ |
| 31. Tretrahydrodiscalamide A potassium salt | $R_1$ = OMe, | $R_2$ = O$^-$K$^+$ |
| 32. Tretrahydrodiscalamide B potassium salt | $R_1$ = OH, | $R_2$ = O$^-$K$^+$ |

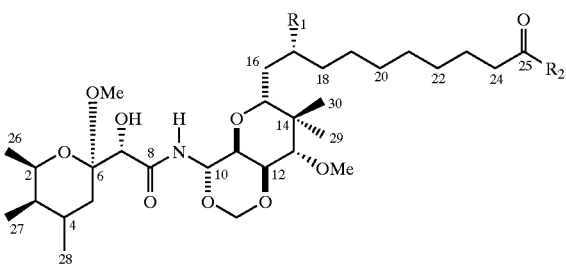

Δ4-28, Δ18, Δ21 or Δ4-28, Δ18, Δ23 or Δ4-28, Δ21
Δ23 or Δ18, Δ21, Δ23

| | | |
|---|---|---|
| 33. Dihydrodiscalamide A | $R_1$ = OMe, | $R_2$ = OH |
| 34. Dihydrodiscalamide B | $R_1$ = OH, | $R_2$ = OH |
| 35. Dihydrodiscalamide A methylester | $R_1$ = OMe, | $R_2$ = OMe |
| 36. Dihydrodiscalamide B methylester | $R_1$ = OH, | $R_2$ = OMe |
| 37. Dihydrodiscalamide A sodium salt | $R_1$ = OMe, | $R_2$ = O$^-$Na$^+$ |
| 38. Dihydrodiscalamide B sodium salt | $R_1$ = OH, | $R_2$ = O$^-$Na$^+$ |
| 39. Dihydrodiscalamide A potassium salt | $R_1$ = OMe, | $R_2$ = O$^-$K$^+$ |
| 40. Dihydrodiscalamide B potassium salt | $R_1$ = OH, | $R_2$ = O$^-$K$^+$. |

As would be appreciated by one skilled in the art, double bonds located in the structures set forth herein are denoted by the "Δ" symbol. Thus, for example, the hexahydrodiscalamide compounds, exemplified above as compounds 17 through 24, each have one double bond at one of the following positions 4–28, 18, 21, or 23.

Acylation (OH to OCOR) of the compounds of the subject invention can be achieved by treating the compound with a mixture of alkyl anhydride and pyridine (1:1) at room temperature overnight or maintaining at 60° C. for ~4 hours. Hydrogenation can be achieved by shaking the compound in ethanol in an atmosphere of $H_2$ at 50 psi in the presence of the catalyst 10% vanadium on activated carbon. The conversion of (COOA to $CH_2OH$, where A=lower alkyls) can be achieved by treating the compound with LiAlH$_4$ in THF at 5° C.

Additional suggested methods for the preparation of discalamide A analogs are as follows:
1. Hydrogenation: $H_2/PtO_2$, EtOH, r.t., 3–12 h
2. Acetylation: (i) Ac$_2$O, or AcCl, Pyr, DMAP, 1–40 h; (ii) Ac$_2$O, BF$_3$, Et$_2$O, THF, 0° C.
3. Demethylation at C-6, C-13 and C-17: (i) AcOH, THF, $H_2O$, 45° C., 3–6 h; (ii) $H_3BO_3$, EtOCH$_2$CH$_2$OH, 90° C., 2 h
4. Formation of benzyl ether at C-7; NaH, p-MeOC$_6$H$_4$CH$_2$Cl, THF
5. Amide formation (N,N-Dimethylamide): SOCl$_2$, 70° C., 3 h, Me$_2$NH
6. Chain elongation at the carboxy end using Grignard reagents (RMgX)
7. Chain length reduction using ozonolysis methods The subject invention further pertains to methods of use of the new compounds and compositions of the invention, e.g., methods of improving immune responses and methods of inhibiting tumors and other cancer cells in an animal, preferably a mammal. Most preferably, the invention comprises a method for the antitumor treatment of a human in need of such treatment, ie., a human hosting cancer cells, including breast, colon, CNS, ovarian, renal, prostate, bone, gastrointestinal, stomach, testicular, or lung tumors, or leukemia cells. In addition to the types of cancer cells listed above for which the subject compounds and compositions are particularly useful, the subject compounds can also be used against certain CNS cancer cell lines, melanoma cell lines, ovarian cancer cell lines, renal cancer cell lines, pancreatic cell lines and prostate cancer cell lines.

Materials and Methods

NMR Experiments: $^1$H and 2D NMR spectra were recorded on a 500 MHz and $^{13}$C NMR spectra were measured on a 125.7 MHz spectrometer. All chemical shifts were recorded with respect to the solvent CD$_3$OD, 3.30 ppm.

A more complete understanding of the invention can be obtained by reference to the following specific examples of compounds, compositions, and methods of the invention. The following examples illustrate procedures for practicing the invention. These examples should not be construed as limiting. All percentages are by weight and all solvent mixture proportions are by volume unless otherwise noted. It will be apparent to those skilled in the art that the examples involve use of materials and reagents that are commercially available from known sources, e.g., chemical supply houses, so no details are given respecting them.

EXAMPLE 1

Isolation, Purification and Structure Determination of Discalamide A (I) and Discalamide B (II)

Extraction and Isolation: The concentrated EtOH extract of the sponge (5.6 kg) was partitioned between EtOAc and $H_2O$. The EtOAc soluble fraction that showed cytotoxic activities against P388 and A549 cell lines was fractionated on an open Si gel column using $CH_2Cl_2$ and increasing amount of MeOH. The fractions eluted with 50% MeOH/$CH_2Cl_2$ (1.44 g) were again partitioned between heptane (3×200 ml) and 80% methanol in water (50 ml). The concentrated aqueous methanol fraction (1.09 g) was separated on a reversed-phase C-18 vacuum flash chromatography using a gradient of aqueous methanol as eluent. Fractions 3, 4, 5 and 6 were combined for HPLC purification. Initial HPLC (Hamilton PRP-1, 305×7 mm, 5μ) purification was done by using 85% MeOH in water as eluent followed by another HPLC purification using (Vydac 250×10 mm, 5μ) 40% MeCN in water to give Discalamide A (I) (35.0 mg, 0.00062% wet wt.) and Discalamide B (II) (1.0 mg, 0.000018% wet wt.).

Discalamide A (I) is a white amorphous powder whose molecular formula was deduced as $C_{32}H_{49}O_{11}N$ from HRFABMS [(M+Na)+ m/z 646.3188] and NMR data. The absorption peaks in IR spectrum (KBr film) was indicative of the presence of hydroxyl groups ($v_{max}$ 3387 cm$^{-1}$), an amide carbonyl ($v_{max}$ 1535 cm$^{-1}$) and an acid carbonyl ($v_{max}$ 1680 cm$^{-1}$). A strong UV absorption at $\lambda_{max}$ (MeOH) 254 nm ($\epsilon$28,909) which is characteristic for a diene conjugation of a carbonyl group.

TABLE 2

$^1$H and $^{13}$C NMR data for discalamide A (I) and the long-range connectivities observed in the HMBC experiment (CD$_3$OD).

| Position | $^{13}$C | $^1$H, mult., J (Hz) | HMBC |
|---|---|---|---|
| 2 | 70.9 | 3.86 (m) | C-4, C-6, C-27, C-26 |
| 3 | 43.0 | 2.17 (dd, 2.4, 2.3) | C-5, C-28, C-4, C-27 |
| 4 | 147.9 | — | — |
| 5 | 34.6 | 2.27, 2.36 (dd, 14.0, 14.1) | C-3, C-28, C-7, C-6, C-4 |
| 6 | 101.3 | — | — |
| 7 | 73.5 | 4.22 (s) | C-5, C-6, C-8 |
| 8 | 174.0 | — | — |
| 9 (N—H) | | 7.54 (d, 9.5) | — |
| 10 | 75.3 | 5.60 (d, 8.5) | C-(10-O—C), C-8, C-11 |
| 11 | 70.2 | 3.85 (m) | C13, C-15, C-12 |
| 12 | 74.9 | 4.10 (dd 6.3, 6.1) | C-10, C-(10-O—C), C-13 |
| 13 | 81.1 | 3.45 (d, 9.0) | C-15 |
| 14 | 41.6 | — | — |
| 15 | 77.1 | 3.26 (m) | C-11, C-13, C-17 |
| 16 | 36.2 | 1.44, 1.65 (dddd, 12.1, 11.2, 10.6, 12.1) | C-18, C-17 |
| 17 | 81.6 | 3.54 (ddd, 3.2, 1.6, 3.6) | C-(17-O—C), C-16 |
| 18 | 132.3 | 5.14 (dd, 15.6, 15.4) | C-16, C-20, C-17 |
| 19 | 134.5 | 5.71 (ddd, 13.3, 13.3, 15.4) | C-17, C-21, C-20 |
| 20 | 36.4 | 2.90, 2.91 (d, 4.0) | C-18, C-22, C-21 |
| 21 | 139.8 | 6.05 (ddd, 13.7, 14.7, 15.4) | C-19, C-23, C-18, C-20 |
| 22 | 131.1 | 6.23 (dd, 11.3, 11.8) | C-20, C-24, C-21, C-23 |
| 23 | 142.6 | 7.08 (dd, 11.8, 13.6) | C-21, C-25 |
| 24 | 127.1 | 5.83 (d, 14.6) | C-22 |
| 25 | 175.9 | — | — |
| 26 | 18.2 | 1.15 (d, 6.5) | C-3, C-2 |
| 27 | 12.6 | 0.94 (d, 7.0) | C-2 |
| 28 | 110.9 | 4.60, 4.77 (ss) | C-3, C-5, C-4 |
| 29 | 24.1 | 0.92 (s) | C-13, C-15, C-14 |
| 30 | 15.0 | 0.79 (s) | C-13, C-15 |
| 10-O—CH$_2$ | 87.2 | 4.74, 5.08 (dd, 6.9, 7.0) | C-12, C-10 |
| 6-O—CH$_3$ | 48.6 | 3.20 (s) | C-6 |
| 13-O—CH$_3$ | 61.8 | 3.48 (s) | C-13 |
| 17-OCH$_3$ | 56.1 | 3.13 (s) | C-17 |

Discalamide B (11) is a colorless amorphous solid whose molecular formula was deduced as C$_{31}$H$_{47}$O$_{11}$N from HRFABMS [(M+Na)+ m/z 632.3046] and NMR data. The absorption peaks in IR spectrum (KBr film) was indicative of the presence of hydroxyl groups ($v_{max}$ 3429 cm$^{-1}$), amide carbonyl ($v_{max}$ 1528 cm$^{-1}$) and acid carbonyl ($v_{max}$ 1701 cm$^{-1}$). A strong UV absorption at $\lambda_{max}$ (MeOH) 259 nm ($\epsilon$12667) indicated a diene-conjugated carbonyl group.

TABLE 3

$^1$H and $^{13}$C NMR data for discalamide B (II) and the long-range connectivities observed in the HMBC experiment (10% CD$_3$OD/CDCl$_3$)

| Position | $^{13}$C | $^1$H, mult, J (Hz) | HMBC |
|---|---|---|---|
| 2 | 70.4 | 3.82 (m) | C-4, C-6, C-27, C-26 |
| 3 | 41.4 | 2.09 (dd, 2.5, 2.4) | C-5, C-28, C-4, C-27 |
| 4 | 146.0 | — | — |
| 5 | 33.4 | 2.24, 2.20 (dd, 14.5, 14.4) | C-3, C-28, C-7, C-6, C-4 |
| 6 | 99.8 | — | — |
| 7 | 73.2 | 4.15 (s) | C-5, C-6, C-8 |
| 8 | 172.4 | — | — |
| 9 (N—H) | — | — | |
| 10 | 73.2 | 5.71 (d, 9.6) | C-(10-O—C), C-8, C-11 |
| 11 | 69.5 | 3.80 (m) | C-13, C-15, C-12 |
| 12 | 74.1 | 4.08 (dd 6.6, 6.5) | C-10, C-(10-O—C), C-13 |
| 13 | 79.1 | 3.38 (d, 10.0) | C-15 |
| 14 | 41.2 | — | — |
| 15 | 79.3 | 3.38 (d, 10) | C-11, C-13, C-17 |
| 16 | 35.8 | 1.43 (b) | C-18, C-17 |
| 17 | 73.3 | 3.97 (dd, 7.2, 6.1) | C-(17-O—C), C-16 |
| 18 | 133.2 | 5.29 (dd, 6.6, 6.6) | C-16, C-20, C-17 |
| 19 | 128.3 | 5.54 (ddd, 6.3, 7.4, 6.3) | C-17, C-21, C-20 |
| 20 | 35.1 | 2.75 (dd, 4.0, 3.9) | C-18, C-22, C-21 |
| 21 | 138.4 | 5.88 (ddd, 5.4, 1.6, 6.4) | C-19, C-23, C-18, C-20 |
| 22 | 129.8 | 6.05 (dd, 9.6, 9.4) | C-20, C-24, C-21, C-23 |
| 23 | 141.7 | 6.98 (b) | C-21, C-25 |
| 24 | 128.3 | 5.71 (d, 9.6) | C-22 |
| 25 | 168.8 | — | — |
| 26 | 17.7 | 1.07 (d, 6.6) | C-3, C-2 |
| 27 | 11.7 | 0.86 (d, 3.8) | C-2 |
| 28 | 109.9 | 4.72, 4.58 (ss) | C-3, C-5, C-4 |
| 29 | 23.0 | 0.85 (s) | C-13, C-15, C-14 |
| 30 | 13.5 | 0.75 (s) | C-13, C-15 |
| 10-O—CH$_2$ | 86.6 | 5.03, 4.70 (dd, 6.9, 7.0) | C-12, C-10 |
| 6-O—CH$_3$ | 48.3 | 3.15 (s) | C-6 |
| 13-O—CH$_3$ | 61.6 | 3.41 (s) | C-13 |

EXAMPLE 2

Methylation of Discalamide A (I)

Discalamide A (2 mg) in MeOH (0.5 ml) was treated with an excess of CH$_2$N$_2$ in ether at ice-cold temperature for 2 h in a screw-capped vial. The reaction mixture was dried under a stream of nitrogen and purification by HPLC (Lichrosorb 5$\mu$ Silica, 10×250-mm Phenomenex column) using 3% MeOH/CH$_2$Cl$_2$ as the mobile phase, gave Discalamide A methylester (III) (1.6 mg): HRFABMS of [M+H]+ m/z 638.3470 for C$_{33}$H$_{51}$NO$_{11}$ (calcd. 638.3540). Colorless gum UV $\lambda_{max}$ (MeOH) 261 nm ($\epsilon$18867); IR (KBr) 3350, 1688, 1528 cm$^{-1}$. $^1$H NMR (CD$_3$OD): See Table 4.

TABLE 4

$^1$H and $^{13}$C NMR data for discalamide A methylester (III) and its multiplicities in CD$_3$OD.

| Position | $^{13}$C | $^1$H, mult., J (Hz) |
|---|---|---|
| 2 | 70.9 | 3.92 (m) |
| 3 | 43.0 | 2.21 (dd, 2.4, 2.d) |
| 4 | 148.0 | — |
| 5 | 34.7 | 2.31, 2.41 (dd, 14.1, 14.3) |
| 6 | 101.3 | — |
| 7 | 73.7 | 4.25 (s) |
| 8 | 174.2 | — |
| 9 (N—H) | — | — |
| 10 | 75.2 | 5.63 (d, 8.8) |
| 11 | 70.2 | 3.89 (m) |
| 12 | 75.0 | 4.14 (dd 6.3, 6.4) |
| 13 | 81.0 | 3.48 (d, 9.3) |
| 14 | 41.7 | — |
| 15 | 77.0 | 3.26 (b) |
| 16 | 36.5 | 1.47, 1.69 (mdd, 10.1, 5.8) |
| 17 | 81.6 | 3.55 (ddd, 1.7, 2.4, 2.5) |
| 18 | 132.7 | 5.22 (ddd, 5.5, 8.4, 8.4) |
| 19 | 134.1 | 5.74 (ddd, 2.0, 6.5, 7.6) |
| 20 | 36.1 | 2.99 (dd, 6.0, 6.5) |
| 21 | 143.7 | 6.28 (m) |

TABLE 4-continued $^1$H and $^{13}$C NMR data for discalamide A methylester (III) and its multiplicities in CD$_3$OD.

| Position | $^{13}$C | $^1$H, mult., J (Hz) |
| --- | --- | --- |
| 22 | 130.3 | 6.34 (m) |
| 23 | 146.6 | 7.32 (dd, 10.2, 10.4) |
| 24 | 120.4 | 5.88 (d, 15.4) |
| 25 | 169.3 | — |
| 26 | 18.1 | 1.18 (d, 9.9) |
| 27 | 12.5 | 0.98 (d, 7.8) |
| 28 | 110.3 | 4.64 (s), 4.85 (s) |
| 29 | 24.0 | 0.96 (s) |
| 30 | 14.9 | 0.83 (s) |
| 10-O—CH$_2$ | 87.2 | 4.78, 5.12 (dd, 6.8, 6.8) |
| 6-O—CH$_3$ | 48.5 | 3.25 (s) |
| 13-O—CH$_3$ | 61.8 | 3.51 (s) |
| 17-OCH$_3$ | 56.1 | 3.17 (s) |
| 25-OCH$_3$ | 52.0 | 3.70 (s) |

EXAMPLE 3

P388 and A549 Cytotoxicity Assays

Compounds were analyzed as to their effects on proliferation of A549 human lung adenocarcinoma and P388 murine leukemia cell lines. P388 cells were obtained from Dr. R. Camalier, National Cancer Institute, Bethesda, Md., and A549 cells were obtained from American Type Culture Collection, Rockville, Md. All cell lines were maintained in Roswell Park Memorial Institute (RPMI) medium 1640 supplemented with 100 U/ml penicillin, 100 mg/ml streptomycin, 60 mg/ml 1-glutamine, 18 mM HEPES, 0.05 mg/ml gentamicin (Life Technologies, Gaithersburg, Md.) and 10% fetal bovine serum and cultured in plastic tissue culture flasks at 37° C. in humidified air containing 5% $CO_2$. Stock cultures of P388 cells were subcultured 1:20 in fresh tissue culture medium (TCM) every 2 to 3 days. Stock cultures of A549 cells were subcultured 1:10 every 3 to 4 days.

To assess the antiproliferative effects of agents against P388 cells, 200 µl cultures (96-well tissue culture plates, Nunc, Denmark) were established at $2 \times 10^4$ cells/ml in TCM or TCM containing the test agent at 0.03–5.0 µg/ml. After 48 hours exposure, P388 cells were enumerated using 3-[4,5-dimethylthiazol-2-yl]-2,5-diphenyltetrazolium bromide (MTT) as described in the literature (Alley, M. D. et al. [1988] Cancer Res. 48:589). A549 cells were enumerated in the same manner using 200 µl cultures established at $3 \times 10^4$ cells/ml and exposing the cultures to the test agents for 72 hours. The results were expressed as percent inhibition compared to the negative (no drug) control. Positive drug controls of varying dilutions of 5-fluorouracil and adriamycin (Sigma Chemical Co., St. Louis, Mo.) were included to monitor drug sensitivity of the cell line.

To quantitate the effects of compounds on cell proliferation and resulting $IC_{50}$ values, 75 µl of warm growth media containing 5 mg/ml MTT is added to each well, cultures returned to the incubator, and left undisturbed for 3 hours. To spectrophotometrically quantitate formation of reduced formazan, plates are centrifuged (500×g, 10 minutes), culture fluids removed by aspiration, and 200 µl of acidified isopropanol (2 ml concentrated HC1/liter isopropanol) added per well. The absorbance of the resulting solutions is measured in a plate reader (Tecan Spectra SLT; TECAN U.S., Research Triangle Park, NC) at 570 nm with a 650 nm reference filter. The absorbance of tests wells is divided by the absorbance of drug-free wells, and the concentration of agent that results in 50% of the absorbance of untreated cultures ($IC_{50}$) is determined by linear regression of logit-transformed data (Finney, D. J. [1978] Statistical Method in Biological Assay, third ed., pp.316–348, Charles Griffin Co., London). A linear relationship between tumor cell number and formazan production has been routinely observed over the range of cell densities observed in these experiments. The two standard drug controls (indicated above) are included in each assay as a check to monitor the drug sensitivity of each of the cell lines and $IC_{50}$ values are determined for each drug-cell combination.

The results of the bioassays are shown above in Table 1.

EXAMPLE 4

Antiproliferative Effects of Discalamide A on Various Human Tumor Cell Lines

Figure 3A:
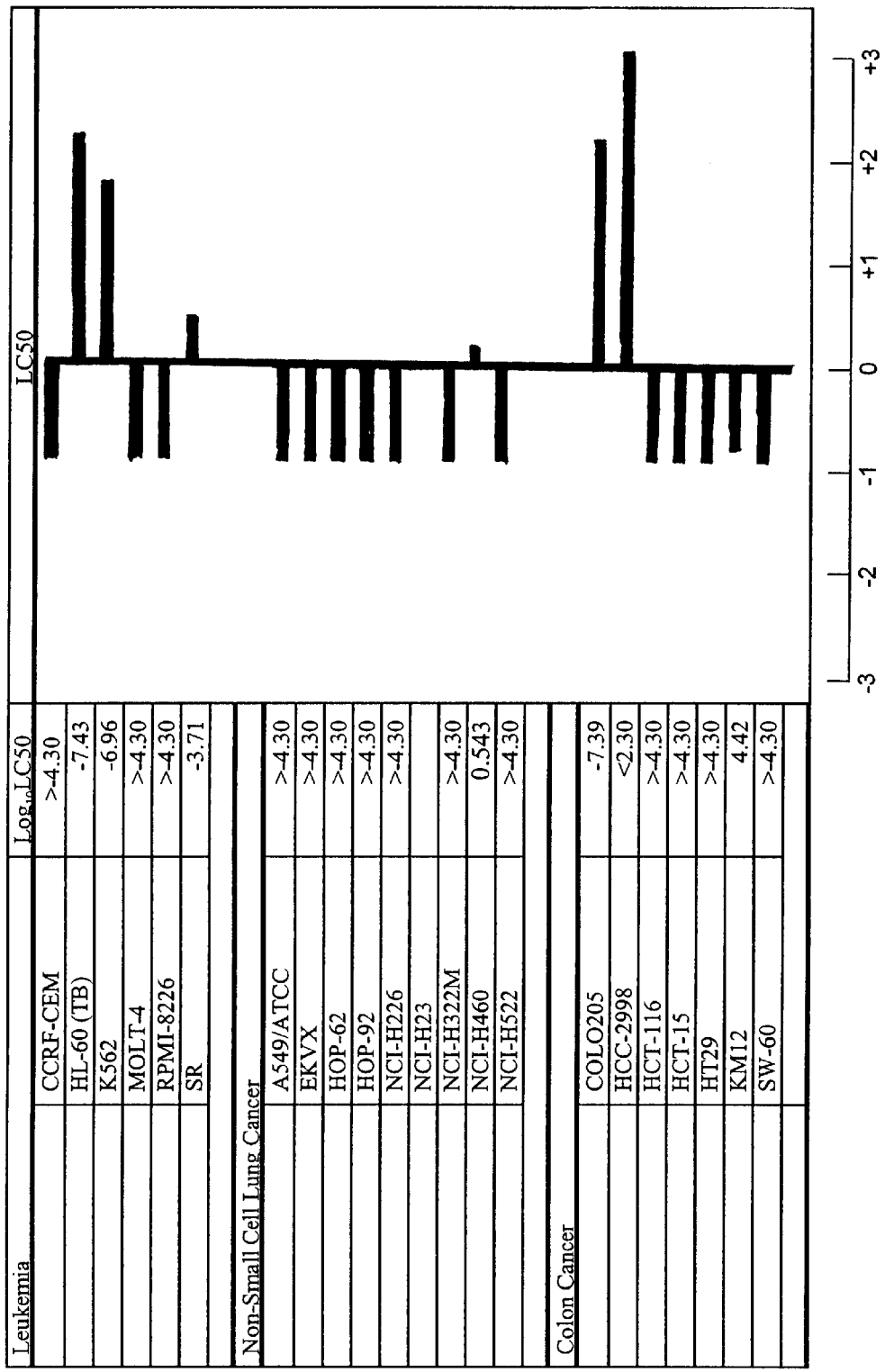
FIGS. 3A–3C show the anti-proliferative effects of discalamide A on various human tumor cell lines.
Figure 3B:
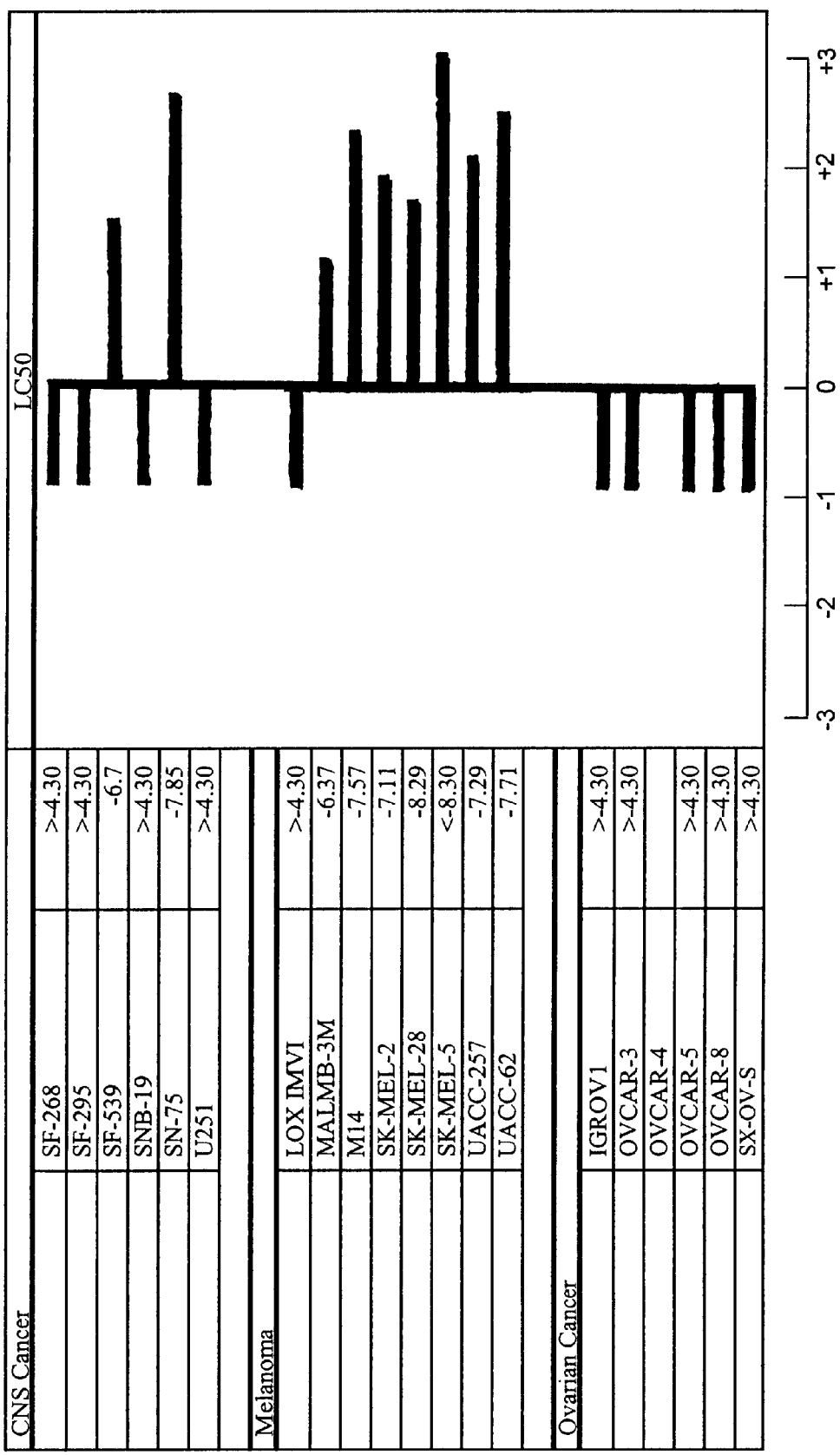
Figure 3C:
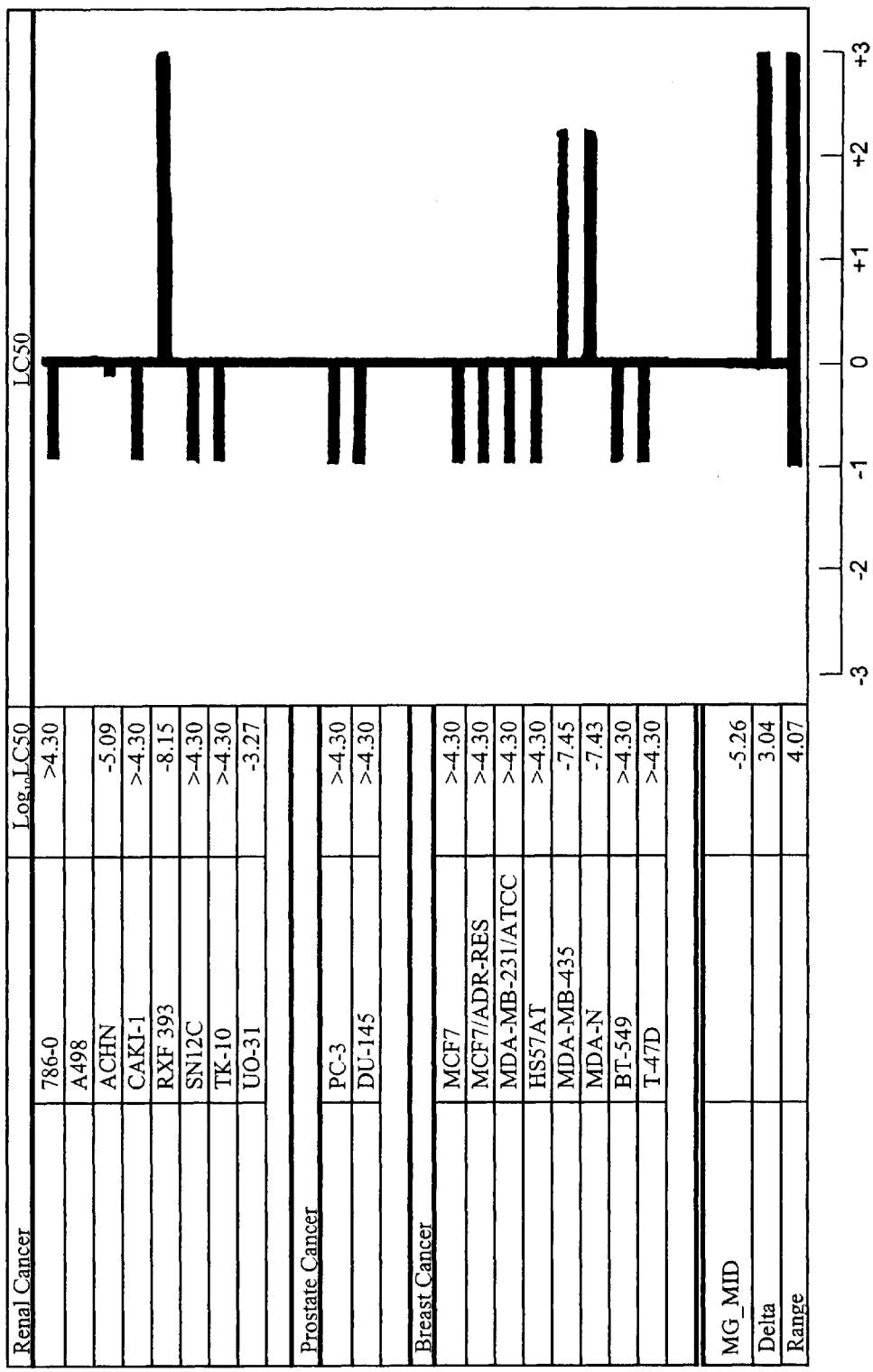

Discalamide A was additionally evaluated for its antiproliferative effects utilizing the National Cancer Institute's in vitro tumor cell line panel. The results of these analyses are shown in the mean graphs presented as FIG. 3. The data are presented using known and accepted measurements of "lethal concentration-50" ($LC_{50}$) where 50% of the cells are killed. Of the approximately 60 cell lines tested, discalamide A demonstrated selective cytotoxicity (as indicated by the bars of the right of the midline) for 16 cell lines. According to $LC_{50}$ measurements for the NCI cell lines, the subject compound tested was particularly effective against two out of six human leukemia (HL-60(TB) and K562), two out of seven human colon cancer (COLO 205 and HCC-2998), two out of six human CNS cancer (SF-295 and SNB-19), seven out of eight human melanoma (LOX IMVI, MALME-3M, M14, SK-MEL-2, SK-MEL-28, SK-MEL-5, and UACC-257), one out of eight human renal cancer (CAKI-1), and two out of eight human breast cancer (HS578T and MDA-MB-231/ATCC) cell lines.

EXAMPLE 5

Formulation and Administration

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

It should be understood that the examples and embodiments described herein are for illustrative purposes only and that various modifications or changes in light thereof will be suggested to persons skilled in the art and are to be included within the spirit and purview of this application and the scope of the appended claims.

We claim:
1. A method for inhibiting the growth of cancer cells, said method comprising administering to said cells an effective amount of a compound having one of the following structures, or an analog thereof:

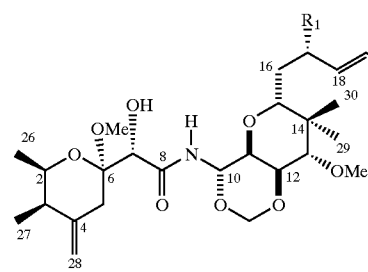

wherein $R_1$=OX, where X=—A, —CH$_2$—Q, —COA or —COZ
$R_2$=OA
A=lower alkyl
Q=phenyl, tolyl or xylyl
Z=monocyclic aryl; or

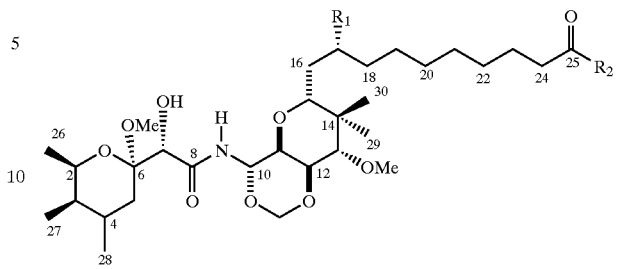

wherein
$R_1$=OX, where X=—A, —CH$_2$—Q, —COA or —COZ
$R_2$=OA
A=lower alkyl
Q=phenyl, tolyl or xylyl
Z=monocyclic aryl; or

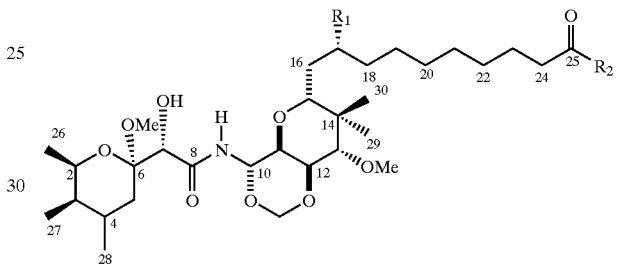

Δ4–28 or Δ18 or Δ21 or Δ23 wherein
$R_1$=OX, where X=—A, —CH$_2$—Q, —COA or —COZ
$R_2$=OA
A=lower alkyl
Q=phenyl, tolyl or xylyl
Z=monocyclic aryl; or

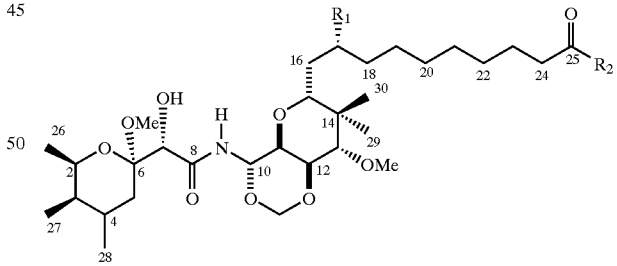

Δ4–28 and Δ18 or Δ4–28 and Δ21 or Δ4–28 and Δ23

Δ18 and Δ21 or Δ18 and Δ23 or Δ21 and Δ23 wherein
$R_1$=OX, where X=—A, —CH$_2$—Q, —COA or —COZ
$R_2$=OA
A=lower alkyl
Q=phenyl, tolyl or xylyl
Z=monocyclic aryl; or

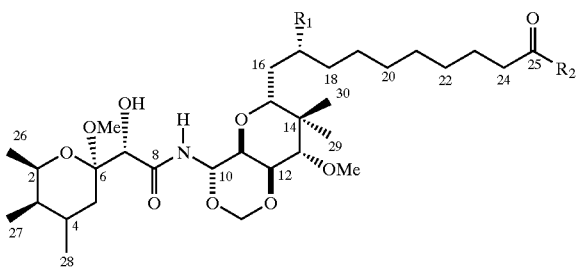

Δ4–28, Δ18, Δ21 or Δ4–28, Δ18, Δ23 or Δ4–28, Δ21,
Δ23 or Δ18, Δ21, Δ23 wherein
$R_1$=OX, where X=—A, —CH$_2$—Q, —COA or —COZ
$R_2$=OA
A=lower alkyl
Q=phenyl, tolyl or xylyl
Z=monocylic aryl.

2. The method, according to claim 1, wherein said compound is selected from the group consisting of:

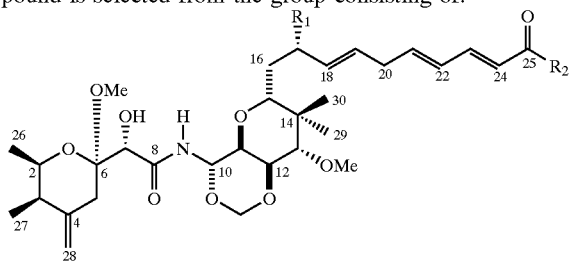

| | | |
|---|---|---|
| a. Discalamide A | $R_1$ = OMe, | $R_2$ = OH |
| b. Discalamide B | $R_1$ = OH, | $R_2$ = OH |
| c. Discalamide A methylester | $R_1$ = OMe, | $R_2$ = OMe |
| d. Discalamide B methylester | $R_1$ = OH, | $R_2$ = OMe |
| e. Discalamide A sodium salt | $R_1$ = OMe, | $R_2$ = O$^-$Na$^+$ |
| f. Discalamide B sodium salt | $R_1$ = OH, | $R_2$ = O$^-$Na$^+$ |
| g. Discalamide A potassium salt | $R_1$ = OMe, | $R_2$ = O$^-$K$^+$ ; and |
| h. Discalamide B potassium salt | $R_1$ = OH, | $R_2$ = O$^-$K$^+$. |

3. The method, according to claim 1, wherein said compound is selected from the group consisting of

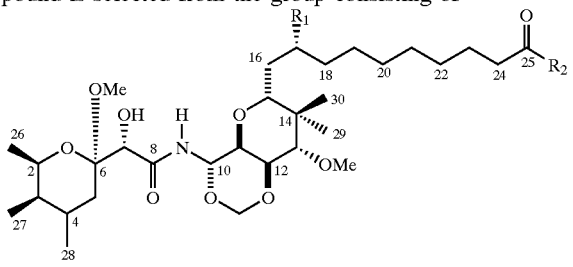

| | | |
|---|---|---|
| a. Octahydrodiscalamide A | $R_1$ = OMe, | $R_2$ = OH |
| b. Octahydrodiscalamide B | $R_1$ = OH, | $R_2$ = OH |
| c. Octahydrodiscalamide A methylester | $R_1$ = OMe, | $R_2$ = OMe |
| d. Octahydrodiscalamide B methylester | $R_1$ = OH, | $R_2$ = OMe |
| e. Octahydrodiscalamide A sodium salt | $R_1$ = OMe, | $R_2$ = O$^-$Na$^+$ |
| f. Octahydrodiscalamide B sodium salt | $R_1$ = OH, | $R_2$ = O$^-$Na$^+$ |
| g. Octahydrodiscalamide A potassium salt | $R_1$ = OMe, | $R_2$ = O$^-$K$^+$; and |
| h. Octahydrodiscalamide B potassium salt | $R_1$ = OH, | $R_2$ = O$^-$K$^+$. |

4. The method, according to claim 1, wherein said compound is selected from the group consisting of

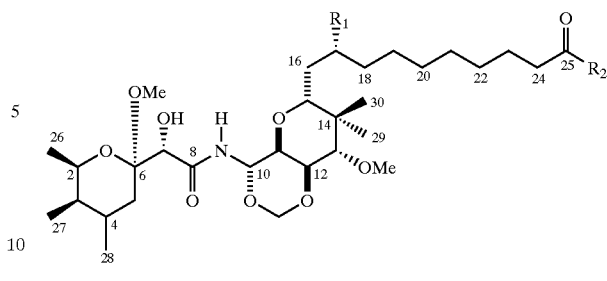

Δ4-28 or Δ18 or Δ21 or Δ23

| | |
|---|---|
| a. Hexahydrodiscalamide A | $R_1$ = OMe, $R_2$ = OH |
| b. Hexahydrodiscalamide B | $R_1$ = OH, $R_2$ = OH |
| c. Hexahydrodiscalamide A methylester | $R_1$ = OMe, $R_2$ = OMe |
| d. Hexahydrodiscalamide B methylester | $R_1$ = OH, $R_2$ = OMe |
| e. Hexahydrodiscalamide A sodium salt | $R_1$ = OMe, $R_2$ = O$^-$Na$^+$ |
| f. Hexahydrodiscalamide B sodium salt | $R_1$ = OH, $R_2$ = O$^-$Na$^+$ |
| g. Hexahydrodiscalamide A potassium salt | $R_1$ = OMe, $R_2$ = O$^-$K$^+$; and |
| h. Hexahydrodiscalamide B potassium salt | $R_1$ = OH, $R_2$ = O$^-$K$^+$. |

5. The method, according to claim 1, wherein said compound is selected from the group consisting of:

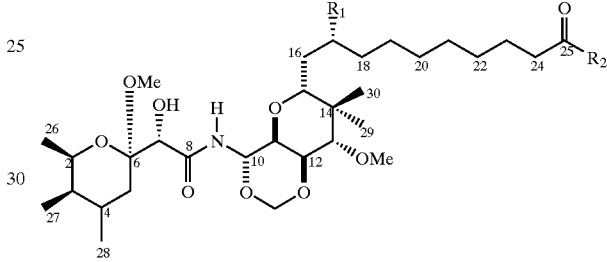

Δ 4-28 and Δ 18 or Δ 4-28 and Δ 21 or Δ 4-28 and Δ23
Δ 18 and Δ 21 or Δ 18 and Δ 23 or Δ 21 and Δ 23

| | |
|---|---|
| a. Tetrahydrodiscalamide A | $R_1$ = OMe, $R_2$ = OH |
| b. Tetrahydrodiscalamide A methylester | $R_1$ = OMe, $R_2$ = OMe |
| c. Tetrahydrodiscalamide B methylester | $R_1$ = OH, $R_2$ = OMe |
| d. Tetrahydrodiscalamide A sodium salt | $R_1$ = OMe, $R_2$ = O$^-$Na$^+$ |
| e. Tetrahydrodiscalamide B sodium salt | $R_1$ = OH, $R_2$ = O$^-$Na$^+$ |
| f. Tetrahydrodiscalamide A potassium salt | $R_1$ = OMe, $R_2$ = O$^-$K$^+$; and |
| g. Tetrahydrodiscalamide B potassium salt | $R_1$ = OH, $R_2$ = O$^-$K$^+$. |

6. The method, according to claim 1, wherein said compound is selected from the group consisting of:

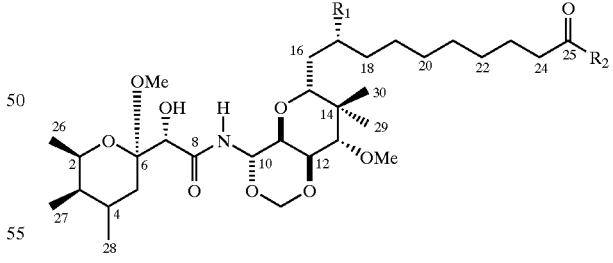

Δ4-28, Δ18, Δ21 or Δ4-28, Δ18, Δ23 or Δ4-28, Δ21
Δ23 or Δ18, Δ21, Δ23

| | |
|---|---|
| a. Dihydrodiscalamide A | $R_1$ = OMe, $R_2$ = OH |
| b. Dihydrodiscalamide B | $R_1$ = OH, $R_2$ = OH |
| c. Dihydrodiscalamide A methylester | $R_1$ = OMe, $R_2$ = OMe |
| d. Dihydrodiscalamide B methylester | $R_1$ = OH, $R_2$ = OMe |
| e. Dihydrodiscalamide A sodium salt | $R_1$ = OMe, $R_2$ = O$^-$Na$^+$ |
| f. Dihydrodiscalamide B sodium salt | $R_1$ = OH, $R_2$ = O$^-$Na$^+$ |
| g. Dihydrodiscalamide A potassium salt | $R_1$ = OMe, $R_2$ = O$^-$K$^+$; and |
| h. Dihydrodiscalamide B potassium salt | $R_1$ = OH, $R_2$ = O$^-$K$^+$. |

7. The method, according to claim 1, wherein said compound is discalamide A, or an analog thereof.

8. The method, according to claim 1, wherein said compound is discalamide A.

9. The method, according to claim 1, wherein said compound is discalamide A-methylester.

10. The method, according to claim 1, wherein said compound is discalamide B.

11. The method, according to claim 1, wherein said cancer cells are selected from the group consisting of human leukemia, lung cancer, colon cancer, CNS cancer, melanoma, ovarian cancer, renal cancer, prostate cancer, breast cancer, bone cancer, gastrointestinal cancer, stomach cancer, and testicular cancer.

12. A compound for inhibiting the growth of cancer cells, said compound comprising administering to said cells an effective amount of a compound having one of the following structures, or an analog thereof:

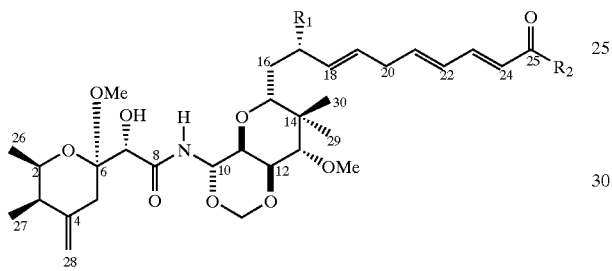

wherein $R_1$=OX, where X=—A, —CH$_2$—Q, —COA or —COZ
$R_2$=OA
A=lower alkyl
Q=phenyl, tolyl or xylyl
Z=monocyclic aryl; or

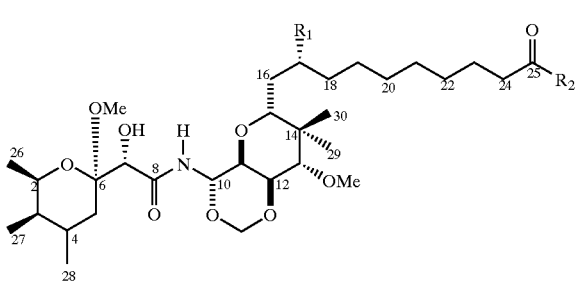

wherein $R_1$=OX, where X=—A, —CH$_2$—Q, —COA or —COZ
$R_2$=OA
A=lower alkyl
Q=phenyl, tolyl or xylyl
Z=monocyclic aryl; or

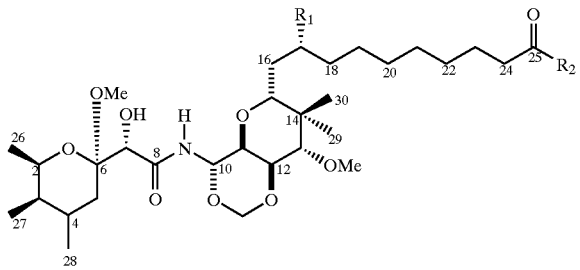

Δ4–28 or Δ18 or Δ21 or Δ23 wherein
$R_1$=OX, where X=—A, —CH$_2$—Q, —COA or —COZ
$R_2$=OA
A=lower alkyl
Q=phenyl, tolyl or xylyl
Z=monocyclic aryl;or

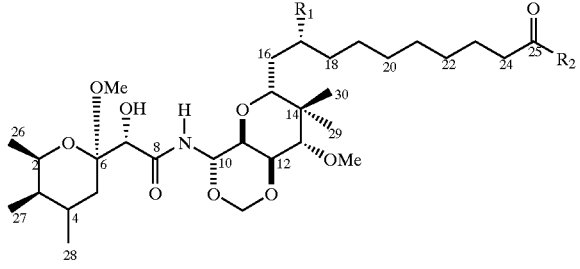

Δ4–28 and Δ18 or Δ4–28 and Δ21 or Δ4–28 and Δ23
Δ18 and Δ21 or Δ18 and Δ23 or Δ21 and Δ23 wherein
$R_1$=OX, where X=—A, —CH$_2$—Q, —COA or —COZ
$R_2$=OA
A=lower alkyl
Q=phenyl, tolyl or xylyl
Z=monocyclic aryl; or Δ4–28, Δ18, Δ21 or Δ4–28, Δ18, Δ23 or Δ4–28, Δ21, Δ23 or Δ18, Δ21, Δ23 wherein
$R_1$=OX, where X=—A, —CH$_2$—Q, or —COA or —COZ

R₂=OA
A=lower alkyl
Q=phenyl, tolyl or xylyl
Z=monocylic aryl.

13. The compound, according to claim 12, wherein said compound is selected from the group consisting of:

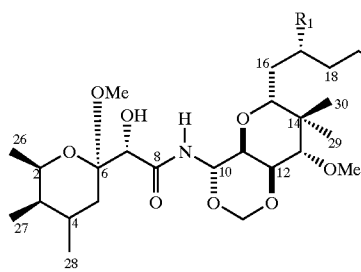

Δ 4-28 and Δ 18 or Δ 4-28 and Δ 21 or Δ 4-28 and Δ23
Δ 18 and Δ 21 or Δ 18 and Δ 23 or Δ 21 and Δ 23

| | |
|---|---|
| a. Tetrahydrodiscalamide A | $R_1$ = OMe, $R_2$ = OH |
| b. Tetrahydrodiscalamide A methylester | $R_1$ = OMe, $R_2$ = OMe |
| c. Tetrahydrodiscalamide B methylester | $R_1$ = OH, $R_2$ = OMe |
| d. Tetrahydrodiscalamide A sodium salt | $R_1$ = OMe, $R_2$ = O⁻Na⁺ |
| e. Tetrahydrodiscalamide B sodium salt | $R_1$ = OH, $R_2$ = O⁻Na⁺ |
| f. Tetrahydrodiscalamide A potassium salt | $R_1$ = OMe, $R_2$ = O⁻K⁺; and |
| g. Tetrahydrodiscalamide B potassium salt | $R_1$ = OH, $R_2$ = O⁻K⁺. |

14. The compound, according to claim 12, wherein said compound is selected from the group consisting of:

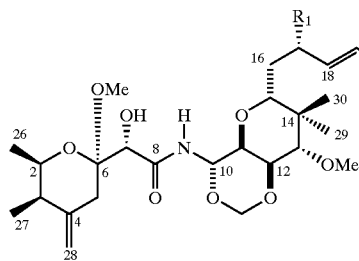

| | |
|---|---|
| a. Discalamide A | $R_1$ = OMe, $R_2$ = OH |
| b. Discalamide B | $R_1$ = OH, $R_2$ = OH |
| c. Discalamide A methylester | $R_1$ = OMe, $R_2$ = OMe |
| d. Discalamide B methylester | $R_1$ = OH, $R_2$ = OMe |
| e. Discalamide A sodium salt | $R_1$ = OMe, $R_2$ = O⁻Na⁺ |
| f. Discalamide B sodium salt | $R_1$ = OH, $R_2$ = O⁻Na⁺ |
| g. Discalamide A potassium salt | $R_1$ = OMe, $R_2$ = O⁻K⁺ ; and |
| h. Discalamide B potassium salt | $R_1$ = OH, $R_2$ = O⁻K⁺. |

15. The compound, according to claim 12, wherein said compound is selected from the group consisting of

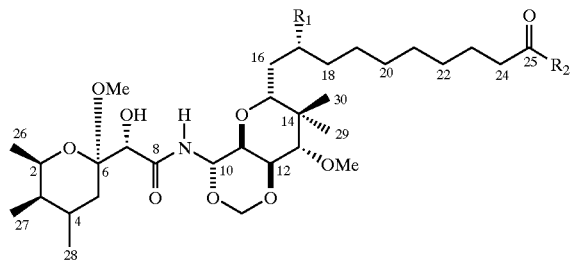

| | |
|---|---|
| a. Octahydrodiscalamide A | $R_1$ = OMe, $R_2$ = OH |
| b. Octahydrodiscalamide B | $R_1$ = OH, $R_2$ = OH |
| c. Octahydrodiscalamide A methylester | $R_1$ = OMe, $R_2$ = OMe |
| d. Octahydrodiscalamide B methylester | $R_1$ = OH, $R_2$ = OMe |
| e. Octahydrodiscalamide A sodium salt | $R_1$ = OMe, $R_2$ = O⁻Na⁺ |
| f. Octahydrodiscalamide B sodium salt | $R_1$ = OH, $R_2$ = O⁻Na⁺ |
| g. Octahydrodiscalamide A potassium salt | $R_1$ = OMe, $R_2$ = O⁻K⁺; and |
| h. Octahydrodiscalamide B potassium salt | $R_1$ = OH, $R_2$ = O⁻K⁺. |

16. The compound, according to claim 12, wherein said compound is selected from the group consisting of

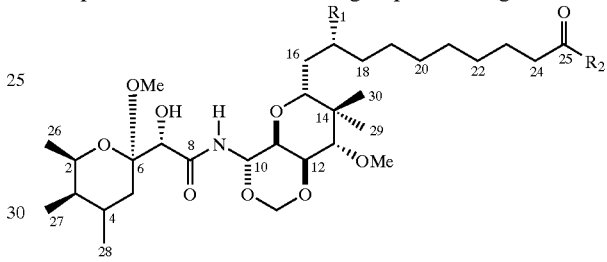

Δ4-28 or Δ18 or Δ21 or Δ23

| | |
|---|---|
| a. Hexahydrodiscalamide A | $R_1$ = OMe, $R_2$ = OH |
| b. Hexahydrodiscalamide B | $R_1$ = OH, $R_2$ = OH |
| c. Hexahydrodiscalamide A methylester | $R_1$ = OMe, $R_2$ = OMe |
| d. Hexahydrodiscalamide B methylester | $R_1$ = OH, $R_2$ = OMe |
| e. Hexahydrodiscalamide A sodium salt | $R_1$ = OMe, $R_2$ = O⁻Na⁺ |
| f. Hexahydrodiscalamide B sodium salt | $R_1$ = OH, $R_2$ = O⁻Na⁺ |
| g. Hexahydrodiscalamide A potassium salt | $R_1$ = OMe, $R_2$ = O⁻K⁺; and |
| h. Hexahydrodiscalamide B potassium salt | $R_1$ = OH, $R_2$ = O⁻K⁺. |

17. The compound, according to claim 12, wherein said compound is selected from the group consisting of

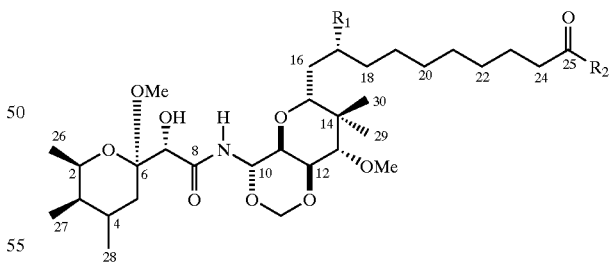

Δ4-28 and Δ18 or Δ4-28 and Δ21 or Δ4-28 and Δ23
Δ18 and Δ21 or Δ18 and Δ23 or Δ21 and Δ23

| | |
|---|---|
| a. Dihydrodiscalamide A | $R_1$ = OMe, $R_2$ = OH |
| b. Dihydrodiscalamide B | $R_1$ = OH, $R_2$ = OH |
| c. Dihydrodiscalamide A methylester | $R_1$ = OMe, $R_2$ = OMe |
| d. Dihydrodiscalamide B methylester | $R_1$ = OH, $R_2$ = OMe |
| e. Dihydrodiscalamide A sodium salt | $R_1$ = OMe, $R_2$ = O⁻Na⁺ |
| f. Dihydrodiscalamide B sodium salt | $R_1$ = OH, $R_2$ = O⁻Na⁺ |
| g. Dihydrodiscalamide A potassium salt | $R_1$ = OMe, $R_2$ = O⁻K⁺; and |
| h. Dihydrodiscalamide B potassium salt | $R_1$ = OH, $R_2$ = O⁻K⁺. |

18. The compound, according to claim 12, wherein said compound is discalamide A, or an analog thereof.

19. The compound, according to claim 12, wherein said compound is discalamide A.

20. The compound, according to claim 12, wherein said compound is discalamide A-methyl ester.

21. The compound, according to claim 12, wherein said compound is discalamide B.

22. A pharmaceutical composition for inhibiting the growth of cancer cells, said composition comprising a pharmaceutically-effective carrier and an effective amount of a compound having one of the following structures, or an analog thereof:

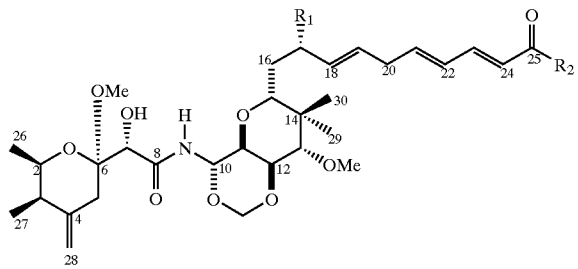

wherein
$R_1$=OX, where X=—A, —CH$_2$—Q, —COA or —COZ
$R_2$=OA
A=lower alkyl
Q=phenyl, tolyl or xylyl
Z=monocyclic aryl; or

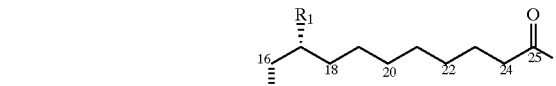

wherein
$R_1$=OX, where X=—A, —CH$_2$—Q, —COA or —COZ
$R_2$=OA
A=lower alkyl
Q=phenyl, tolyl or xylyl
Z=monocyclic aryl; or

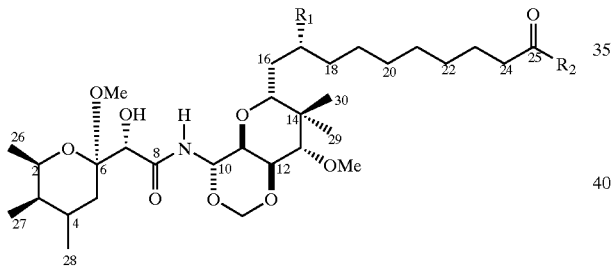

Δ4–28 or Δ18 or Δ21 or Δ23 wherein
$R_1$=OX, where X=—A, —CH$_2$—Q, —COA or —COZ
$R_2$=OA
A=lower alkyl
Q=phenyl, tolyl or xylyl
Z=monocyclic aryl; or

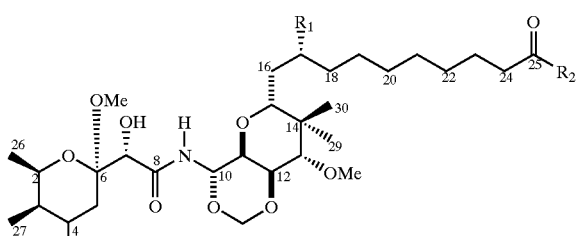

Δ4–28 and Δ18 or Δ4–28 and Δ21 or Δ4–28 and Δ23

Δ18 and Δ21 or Δ18 and Δ23 or Δ21 and Δ23 wherein
$R_1$=OX, where X=—A, —CH$_2$—Q, —COA or —COZ
$R_2$=OA
A=lower alkyl
Q=phenyl, tolyl or xylyl
Z=monocyclic aryl; or

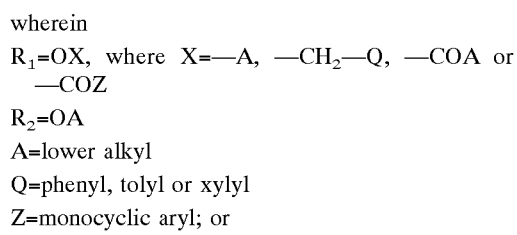

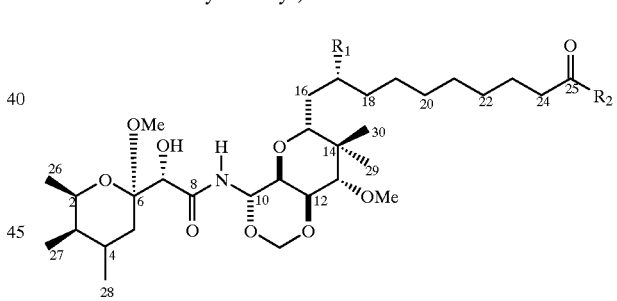

Δ4–28, Δ18, Δ21 or Δ4–28, Δ18, Δ23 or Δ4–28, Δ21,

Δ23 or Δ18, Δ21, Δ23 wherein
$R_1$=OX, where X=—A, —CH$_2$—Q, —COA or —COZ
$R_2$=OA
A=lower alkyl
Q=phenyl, tolyl or xylyl
Z=monocyclic aryl.

23. The composition, according to claim 21, wherein said compound is selected from the group consisting of:

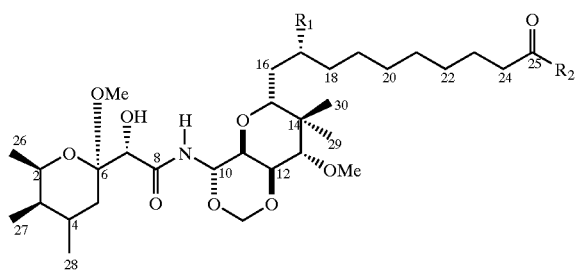

Δ 4-28 and Δ 18 or Δ 4-28 and Δ 21 or Δ 4-28 and Δ23
Δ 18 and Δ 21 or Δ 18 and Δ 23 or Δ 21 and Δ 23

| | |
|---|---|
| a. Tetrahydrodiscalamide A | $R_1$ = OMe, $R_2$ = OH |
| b. Tetrahydrodiscalamide A methylester | $R_1$ = OMe, $R_2$ = OMe |
| c. Tetrahydrodiscalamide B methylester | $R_1$ = OH, $R_2$ = OMe |
| d. Tetrahydrodiscalamide A sodium salt | $R_1$ = OMe, $R_2$ = O$^-$Na$^+$ |
| e. Tetrahydrodiscalamide B sodium salt | $R_1$ = OH, $R_2$ = O$^-$Na$^+$ |
| f. Tetrahydrodiscalamide A potassium salt | $R_1$ = OMe, $R_2$ = O$^-$K$^+$; and |
| g. Tetrahydrodiscalamide B potassium salt | $R_1$ = OH, $R_2$ = O$^-$K$^+$. |

24. The pharmaceutical composition, according to claim 22, wherein said compound is selected from the group consisting of:

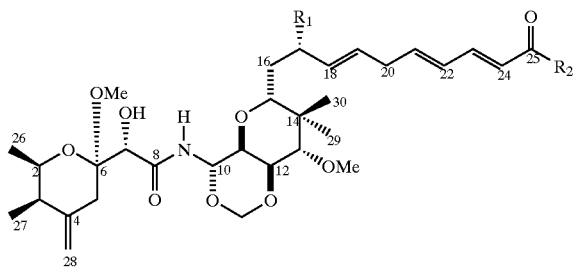

| | |
|---|---|
| a. Discalamide A | $R_1$ = OMe, $R_2$ = OH |
| b. Discalamide B | $R_1$ = OH, $R_2$ = OH |
| c. Discalamide A methylester | $R_1$ = OMe, $R_2$ = OMe |
| d. Discalamide B methylester | $R_1$ = OH, $R_2$ = OMe |
| e. Discalamide A sodium salt | $R_1$ = OMe, $R_2$ = O$^-$Na$^+$ |
| f. Discalamide B sodium salt | $R_1$ = OH, $R_2$ = O$^-$Na$^+$ |
| g. Discalamide A potassium salt | $R_1$ = OMe, $R_2$ = O$^-$K$^+$; and |
| h. Discalamde B potassium salt | $R_1$ = OH, $R_2$ = O$^-$K$^+$. |

25. The pharmaceutical composition, according to claim 22, wherein said compound is selected from the group consisting of

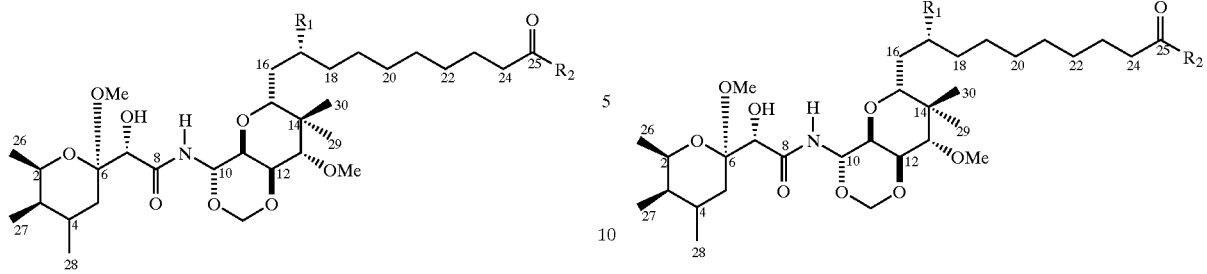

| | |
|---|---|
| a. Octahydrodiscalamide A | $R_1$ = OMe, $R_2$ = OH |
| b. Octahydrodiscalamide B | $R_1$ = OH, $R_2$ = OH |
| c. Octahydrodiscalamide A methylester | $R_1$ = OMe, $R_2$ = OMe |
| d. Octahydrodiscalamide B methylester | $R_1$ = OH, $R_2$ = OMe |
| e. Octahydrodiscalamide A sodium salt | $R_1$ = OMe, $R_2$ = O$^-$Na$^+$ |
| f. Octahydrodiscalamide B sodium salt | $R_1$ = OH, $R_2$ = O$^-$Na$^+$ |
| g. Octahydrodiscalamide A potassium salt | $R_1$ = OMe, $R_2$ = O$^-$K$^+$; and |
| h. Octahydrodiscalamide B potassium salt | $R_1$ = OH, $R_2$ = O$^-$K$^+$. |

26. The pharmaceutical composition, according to claim 22, wherein said compound is selected from the group consisting of

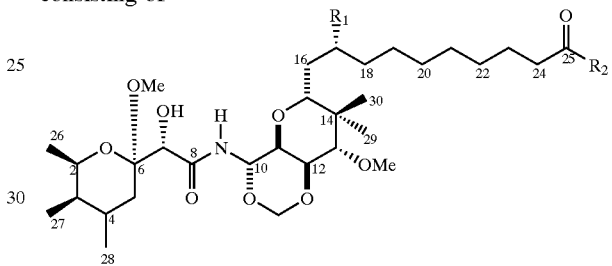

Δ 4-28 or Δ 18 or Δ 21 or Δ23

| | |
|---|---|
| a. Hexahydrodiscalamide A | $R_1$ = OMe, $R_2$ = OH |
| b. Hexahydrodiscalamide B | $R_1$ = OH, $R_2$ = OH |
| c. Hexahydrodiscalamide A methylester | $R_1$ = OMe, $R_2$ = OMe |
| d. Hexahydrodiscalamide B methylester | $R_1$ = OH, $R_2$ = OMe |
| e. Hexahydrodiscalamide A sodium salt | $R_1$ = OMe, $R_2$ = O$^-$Na$^+$ |
| f. Hexahydrodiscalamide B sodium salt | $R_1$ = OH, $R_2$ = O$^-$Na$^+$ |
| g. Hexahydrodiscalamide A potassium salt | $R_1$ = OMe, $R_2$ = O$^-$K$^+$; and |
| h. Hexahydrodiscalamide B potassium salt | $R_1$ = OH, $R_2$ = O$^-$K$^+$. |

27. The pharmaceutical composition, according to claim 22, wherein said compound is selected from the group consisting of

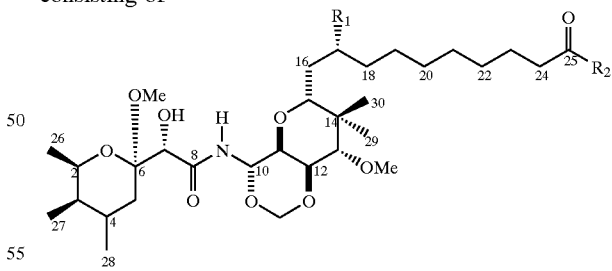

Δ 4-28 and Δ 18 or Δ 4-28 and Δ 21 or Δ 4-28 and Δ23
Δ 18 and Δ 21 or Δ 18 and Δ 23 or Δ 21 and Δ 23

| | |
|---|---|
| a. Dihydrodiscalamide A | $R_1$ = OMe, $R_2$ = OH |
| b. Dihydrodiscalamide B | $R_1$ = OH, $R_2$ = OH |
| c. Dihydrodiscalamide A methylester | $R_1$ = OMe, $R_2$ = OMe |
| d. Dihydrodiscalamide B methylester | $R_1$ = OH, $R_2$ = OMe |
| e. Dihydrodiscalamide A sodium salt | $R_1$ = OMe, $R_2$ = O$^-$Na$^+$ |
| f. Dihydrodiscalamide B sodium salt | $R_1$ = OH, $R_2$ = O$^-$Na$^+$ |
| g. Dihydrodiscalamide A potassium salt | $R_1$ = OMe, $R_2$ = O$^-$K$^+$; and |
| h. Dihydrodiscalamide B potassium salt | $R_1$ = OH, $R_2$ = O$^-$K$^+$. |

28. The pharmaceutical composition, according to claim 22, wherein said compound is discalamide A, or an analog thereof.

29. The pharmaceutical composition, according to claim 22, wherein said compound is discalamide A.

30. The pharmaceutical composition, according to claim 22, wherein said compound is discalamide A-methyl ester.

31. The pharmaceutical composition, according to claim 22, wherein said compound is discalamide B.

32. A method for modulating an immune response in an animal, said method comprising administering to said animal an effective amount of a compound having one of the following structures, or an analog thereof:

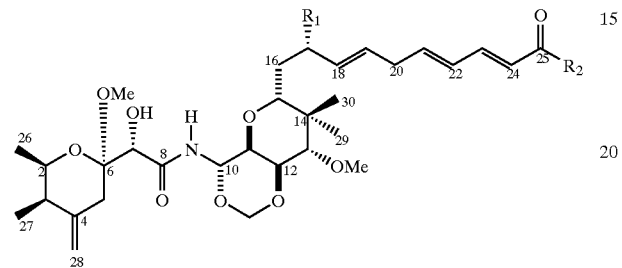

wherein
$R_1$=OX, where X=—A, —CH$_2$—Q, —COA or —COZ
$R_2$=OA
A=lower alkyl
Q=phenyl, tolyl or xylyl
Z=monocyclic aryl; or

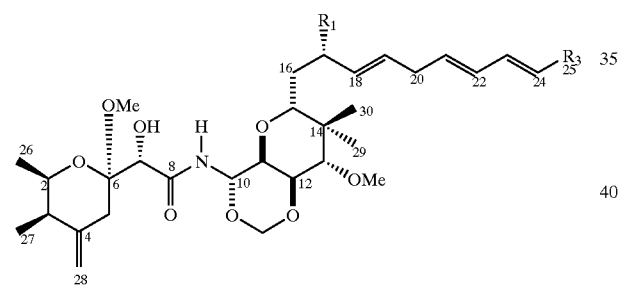

wherein
$R_1$=OX, $R_3$=CH$_2$OX where X=H,A, —CH$_2$—Q, —COA or COZ
A=lower alkyl
Q=phenyl, tolyl or xylyl
Z=monocyclic aryl; or

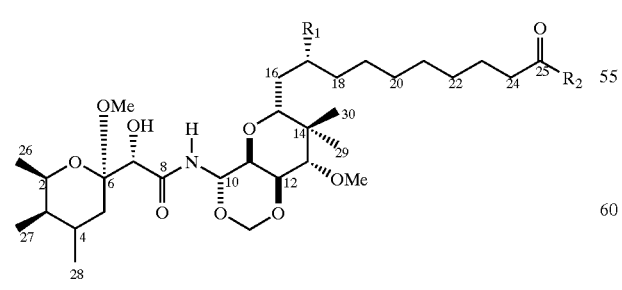

wherein
$R_1$=OX, where X=—A, —CH$_2$—Q, —COA or —COZ
$R_2$=OA
A=lower alkyl
Q=phenyl, tolyl or xylyl
Z=monocyclic aryl; or

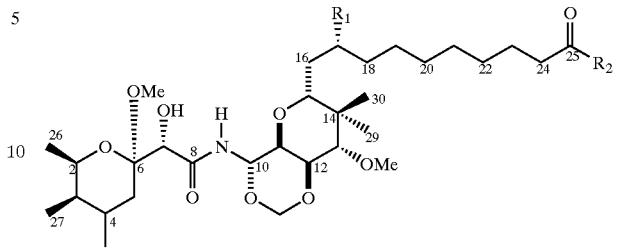

Δ4–28 or Δ18 or Δ21 or Δ23
wherein
$R_1$=OX, where X=—A, —CH$_2$—Q, —COA or —COZ
$R_2$=OA
A=lower alkyl
Q=phenyl, tolyl or xylyl
Z=monocyclic aryl; or

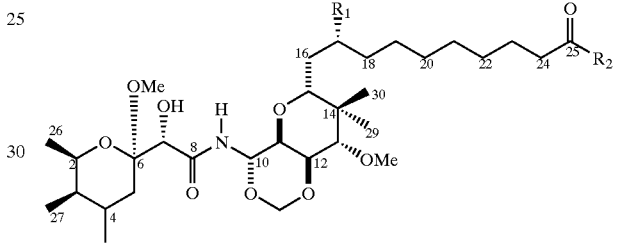

Δ4–28 and Δ18 or Δ4–28 and Δ21 or Δ4–28 and Δ23
Δ18 and Δ21 or Δ18 and Δ23 or Δ21 and Δ23
wherein
$R_1$=OX, where X=—A, —CH$_2$—Q, —COA or —COZ
$R_2$=OA
A=lower alkyl
Q=phenyl, tolyl or xylyl
Z=monocyclic aryl; or

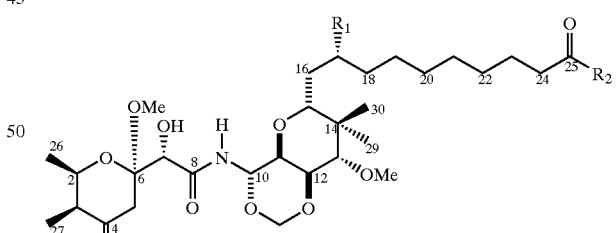

Δ 4-28, Δ 18, Δ 21 or Δ 4-28, Δ 18, Δ 23 or Δ 4-28, Δ 21, Δ 23 or Δ 18, Δ 21, Δ23 wherein
$R_1$=OX, where X=—A, —CH$_2$—Q, —COA or —COZ
$R_2$=OA
A=lower alkyl
Q=phenyl, tolyl or xylyl
Z=monocyclic aryl.

33. The method, according to claim 32, wherein said compound is selected from the group consisting of:

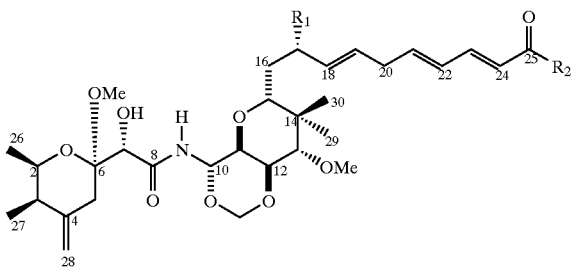

| a. Discalamide A | $R_1$ = OMe, $R_2$ = OH |
| --- | --- |
| b. Discalamide B | $R_1$ = OH, $R_2$ = OH |
| c. Discalamide A methylester | $R_1$ = OMe, $R_2$ = OMe |
| d. Discalamide B methylester | $R_1$ = OH, $R_2$ = OMe |
| e. Discalamide A sodium salt | $R_1$ = OMe, $R_2$ = O$^-$Na$^+$ |
| f. Discalamide B sodium salt | $R_1$ = OH, $R_2$ = O$^-$Na$^+$ |
| g. Discalamide A potassium salt | $R_1$ = OMe, $R_2$ = O$^-$K$^+$; and |
| h. Discalamde B potassium salt | $R_1$ = OH, $R_2$ = O$^-$K$^+$. |

34. The method, according to claim 32, wherein said compound is selected from the group consisting of

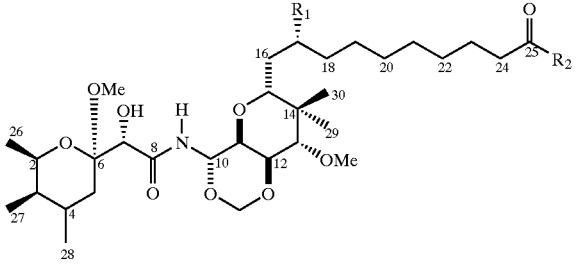

| a. Octahydrodiscalamide A | $R_1$ = OMe, $R_2$ = OH |
| --- | --- |
| b. Octahydrodiscalamide B | $R_1$ = OH, $R_2$ = OH |
| c. Octahydrodiscalamide A methylester | $R_1$ = OMe, $R_2$ = OMe |
| d. Octahydrodiscalamide B methylester | $R_1$ = OH, $R_2$ = OMe |
| e. Octahydrodiscalamide A sodium salt | $R_1$ = OMe, $R_2$ = O$^-$Na$^+$ |
| f. Octahydrodiscalamide B sodium salt | $R_1$ = OH, $R_2$ = O$^-$Na$^+$ |
| g. Octahydrodiscalamide A potassium salt | $R_1$ = OMe, $R_2$ = O$^-$K$^+$; and |
| h. Octahydrodiscalamide B potassium salt | $R_1$ = OH, $R_2$ = O$^-$K$^+$. |

35. The compound, according to claim 32, wherein said compound is selected from the group consisting of

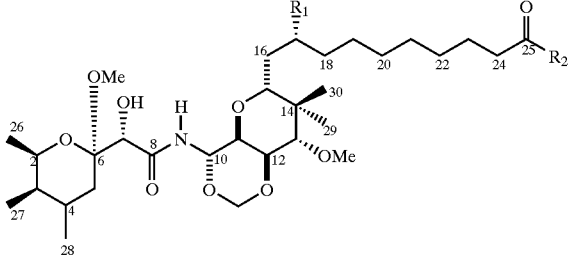

Δ 4-28 or Δ 18 or Δ 21 or Δ23

| a. Hexahydrodiscalamide A | $R_1$ = OMe, $R_2$ = OH |
| --- | --- |
| b. Hexahydrodiscalamide B | $R_1$ = OH, $R_2$ = OH |
| c. Hexahydrodiscalamide A methylester | $R_1$ = OMe, $R_2$ = OMe |
| d. Hexahydrodiscalamide B methylester | $R_1$ = OH, $R_2$ = OMe |
| e. Hexahydrodiscalamide A sodium salt | $R_1$ = OMe, $R_2$ = O$^-$Na$^+$ |
| f. Hexahydrodiscalamide B sodium salt | $R_1$ = OH, $R_2$ = O$^-$Na$^+$ |
| g. Hexahydrodiscalamide A potassium salt | $R_1$ = OMe, $R_2$ = O$^-$K$^+$; and |
| h. Hexahydrodiscalamide B potassium salt | $R_1$ = OH, $R_2$ = O$^-$K$^+$. |

36. The method, according to claim 32, wherein said compound is selected from the group consisting of:

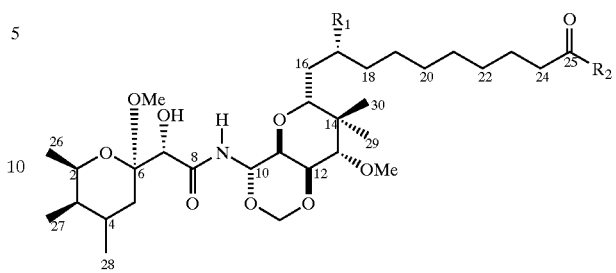

Δ 4-28 and Δ 18 or Δ 4-28 and Δ 21 or Δ 4-28 and Δ23
Δ 18 and Δ 21 or Δ 18 and Δ 23 or Δ 21 and Δ 23

| a. Tetrahydrodiscalamide A | $R_1$ = OMe, $R_2$ = OH |
| --- | --- |
| b. Tetrahydrodiscalamide B | $R_1$ = OH, $R_2$ = OH |
| c. Tetrahydrodiscalamide A methylester | $R_1$ = OMe, $R_2$ = OMe |
| d. Tetrahydrodiscalamide B methylester | $R_1$ = OH, $R_2$ = OMe |
| e. Tetrahydrodiscalamide A sodium salt | $R_1$ = OMe, $R_2$ = O$^-$Na$^+$ |
| f. Tetrahydrodiscalamide B sodium salt | $R_1$ = OH, $R_2$ = O$^-$Na$^+$ |
| g. Tetrahydrodiscalamide A potassium salt | $R_1$ = OMe, $R_2$ = O$^-$K$^+$; and |
| h. Tetrahydrodiscalamide B potassium salt | $R_1$ = OH, $R_2$ = O$^-$K$^+$. |

37. The method, according to claim 32, wherein said compound is selected from the group consisting of:

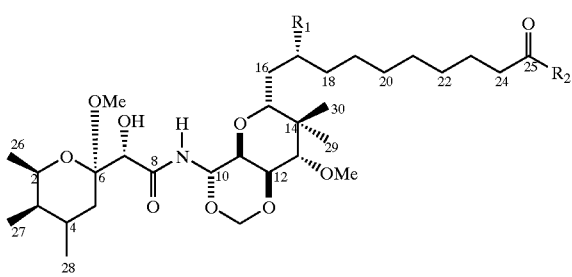

Δ 4-28 and Δ 18 or Δ 4-28 and Δ 21 or Δ 4-28 and Δ23
Δ 18 and Δ 21 or Δ 18 and Δ 23 or Δ 21 and Δ 23

| a. Dihydrodiscalamide A | $R_1$ = OMe, $R_2$ = OH |
| --- | --- |
| b. Dihydrodiscalamide B | $R_1$ = OH, $R_2$ = OH |
| c. Dihydrodiscalamide A methylester | $R_1$ = OMe, $R_2$ = OMe |
| d. Dihydrodiscalamide B methylester | $R_1$ = OH, $R_2$ = OMe |
| e. Dihydrodiscalamide A sodium salt | $R_1$ = OMe, $R_2$ = O$^-$Na$^+$ |
| f. Dihydrodiscalamide B sodium salt | $R_1$ = OH, $R_2$ = O$^-$Na$^+$ |
| g. Dihydrodiscalamide A potassium salt | $R_1$ = OMe, $R_2$ = O$^-$K$^+$; and |
| h. Dihydrodiscalamide B potassium salt | $R_1$ = OH, $R_2$ = O$^-$K$^+$. |

38. The method, according to claim 32, wherein said compound is discalamide A, or an analog thereof.

39. The method, according to claim 32, wherein said compound is discalamide A.

40. The method, according to claim 32, wherein said compound is discalamide A-methylester.

41. The method, according to claim 32, wherein said compound is discalamide B.

* * * * *

UNITED STATES PATENT AND TRADEMARK OFFICE
CERTIFICATE OF CORRECTION

PATENT NO.    : 6,476,065 B2
DATED         : November 5, 2002
INVENTOR(S)   : Sarath P. Gunasekera et al.

Page 1 of 1

It is certified that error appears in the above-identified patent and that said Letters Patent is hereby corrected as shown below:

Column 7,
Line 12, "$\Delta 4\text{-}28$ or $\Delta 18$ or $\Delta 21$ or $\Delta 23$" should read -- $\Delta\ 4\text{-}28$ and $\Delta\ 18$ or $\Delta\ 4\text{-}28$ and $\Delta\ 21$ or $\Delta\ 4\text{-}28$ and $\Delta\ 23$ --

Signed and Sealed this

Twenty-third Day of December, 2003

JAMES E. ROGAN
*Director of the United States Patent and Trademark Office*